US007414032B2

(12) United States Patent
Shiku

(10) Patent No.: US 7,414,032 B2
(45) Date of Patent: Aug. 19, 2008

(54) VACCINE COMPRISING A POLYNUCLEOTIDE ENCODING AN ANTIGEN RECOGNIZED BY A CD4+ HELPER T-CELL AND A POLYNUCLEOTIDE ENCODING A TUMOR SPECIFIC OR ASSOCIATED ANTIGEN RECOGNIZED BY A CD8+ CTL

(75) Inventor: Hiroshi Shiku, Tsu (JP)

(73) Assignee: Immunofrontier, Inc., Tsu-Shi (JP)

( * ) Notice: Subject to any disclaimer, the term of this patent is extended or adjusted under 35 U.S.C. 154(b) by 0 days.

(21) Appl. No.: 10/746,747

(22) Filed: Dec. 23, 2003

(65) Prior Publication Data

US 2004/0198684 A1 Oct. 7, 2004

Related U.S. Application Data

(63) Continuation-in-part of application No. PCT/JP02/05486, filed on Jun. 4, 2002.

(30) Foreign Application Priority Data

Jun. 25, 2001 (JP) ............................. 2001-191334
Dec. 24, 2002 (JP) ............................. 2002-372103

(51) Int. Cl.
*A01K 43/04* (2006.01)
*A61K 31/70* (2006.01)
(52) U.S. Cl. ...................................................... 514/44
(58) Field of Classification Search ................ 536/23.1; 514/44; 424/93.2; 435/320.1
See application file for complete search history.

(56) References Cited

U.S. PATENT DOCUMENTS 6,194,389 B1 * 2/2001 Johnston et al. ................ 514/44
2003/0092162 A1 * 5/2003 Shankara et al. .......... 435/235.1

FOREIGN PATENT DOCUMENTS

| JP | 2000-302692 | 10/2000 |
|---|---|---|
| WO | WO 00/34494 A1 | 6/2000 |
| WO | WO 00/40752 A2 | 7/2000 |
| WO | WO 00/40752 A3 | 7/2000 |
| WO | WO 01/53524 A2 | 7/2001 |
| WO | WO 01/53524 A3 | 7/2001 |
| WO | WO 01/83750 A2 | 11/2001 |
| WO | WO 01/83750 A3 | 11/2001 |

OTHER PUBLICATIONS

Resitfo et al. (2000) The Promise of nucleic acid vaccines. Gene Therapy. 7:89-92.*
McCluskie et al. (1999) Route and Method of Delivery of DNA Vaccine Influence Immune Responses in Mice and Non-Human Primates. Molecular Medicine. 5:287-300.*
Verma et al., Gene therapy-promises, problems and prospects. (1997) Nature. 389:239-242.*
Orkin et al., Report and Reccommendations of the Panel to assess the NIH invextment in Research on Gene Therapy (1998) 1-41.*
Marshall., Gene Therapy's Growing Pains (1995) Science 269:1050-1055.*
Tuting et al. (1998) Co-Delivery of T helper 1-biasing cytokine genes enhances the efficacy of gene gun immunization of mice:studies with the model tumor antigen Beta-galactosidase and the BALB/c Meth A p53 tumor specfic antigen. Gene Therapy 6:629-636.*
Ulmer et al. (1998) Protective CD4+ and Cd8+ T cells against Influenza Virus Induced by Vacination with Nucleoprotein DNA. Journal of Virology 72:5648-5653.*
Chen et al. (2000) Clinical Cancer Research 6 :4381-4388.*
Gnjatic et al. (2000) PNAS 97 :10917-10922.*
Hanke et al. (1999) Vaccine 589-596.*
Gnjatic et al. Strategy for Monitoring T Cell Responses to NY-ESO-1 in Patients with any HLA Class I Allele. PNAS, 2000, vol. 97, No. 20, pp. 10917-10922.*
Chen et al. Induction of Antitumor Immunity with Combination of HER2/neu DNA Vaccine and Interleukin 2 Gene-Modified Turmo Vaccine. Clinical Cancer Res., 2000, vol. 6, pp. 4381-4388.*
Nomura et al. Gene Expression and Antitumor Effects Following Direct Interferon Gamma Gene Transfer with Naked Plasmid DNA and DC-Chol Liposome Complexes in Mice. Gene Therapy, 1999, vol. 6, pp. 121-129.*
Ikeda Hiroaki et al.; "Mutated mitogen-activated protein kinase: A tumor rejection antigen of mouse sarcoma"; *Proc. Nat'l. Acad. Sci. U.S.A.*; Jun. 1997; pp. 6375-6379; vol. 94.
Nishikawa, Hiroyoshi et al.; "Role of SEREX-defined immunogenic wild-type cellular molecules in the development of tumor-specific immunity"; *PNAS*; Dec. 4, 2001; pp. 14571-14576; vol. 98, No. 25.
Nishikawa, Hiroyoshi et al.; *Clinical Immunology (translation)*; 2002; pp. 328-333; vol. 37, No. 3; Japan (in Japanese).
Shiku, Hiroshi; *Gendai Iryo*; 2000; pp. 24-30; vol. 32, No. 5; Japan (in Japanese).
Shiku, Hiroshi; "Peptide vaccine for cancer"; *Tissue Culture (translation)*; 2000; pp. 9-12; vol. 26, No. 1; Japan (in Japanese).
Liu, M.A.; "DNA vaccines: a review"; *Journal of Internal Medicine* 253:402-410 (2003).

(Continued)

*Primary Examiner*—Deborah Crouch
(74) *Attorney, Agent, or Firm*—Townsend and Townsend and Crew LLP

(57) ABSTRACT

The present invention relates to a DNA vaccine for developing tumor-specific immunity. Specifically, the invention relates to a DNA vaccine comprising antigens recognized by CD4+ helper T cells and CD8+ cytotoxic T cells, respectively. Preferably, the antigen recognized by CD4+ helper T cells is a molecule identified by the SEREX method and that recognized by CD8+ cytotoxic T cells is a tumor-specific antigen, tumor-associated antigen or cell-associated antigen. Furthermore, so that the antigens recognized by CD4+ helper T cells and CD8+ CTL are expressed and presented on the same cell, the expression vectors preferably are immobilized on the same gold particle and administered into the cell by gene gun; however, this invention is not restricted thereto. The vaccine can also be used as a pharmaceutical agent.

16 Claims, 6 Drawing Sheets

OTHER PUBLICATIONS

Roy, Michael J. et al.; "Induction of antigen-specific CD8+ T cells, T helper cells, and protective levels of antibody in humans by particle-mediated administration of hepatitis 8 virus DNA vaccine"; *Vaccine* 19:764-778 (2001).

Shiku, Hiroshi et al.; "Development of a cancer vaccine: peptides, proteins, and DNA"; *Cancer Chemother. Pharmacol.*; 2000; pp. S77-S82; vol. 46(Suppl.); Springer Verlag.

Swain, W. F.; "Tolerability and Immune Responses in Humans to a PowderJect DNA Vaccine for Hepatits B"; *Dev. Biol.* 104:115-119 (2000).

Kim, Jong J. et al.; "Molecular and immunological analysis of genetic prostate specific antigen (PSA) vaccine"; *Oncogene*; 1998; pp. 3125-3135; vol. 17; Stockton Press.

King, Catherine A. et al.; "DNA vaccines with single-chain Fv fused to fragment C of tetanus toxin induce protective immunity against lymphoma and myeloma"; *Nature Medicine*; Nov. 1998; pp. 1281-1286; vol. 4, No. 11.

Lachman, Lawrence B. et al.; "DNA vaccination against *neu* reduces breast cancer incidence and metastasis in mice"; *Cancer Gene Therapy*; 2001; pp. 259-268; vol. 8, No. 4; Nature Publishing Group.

Sahin, Ugur et al.; "Human neoplasms elicit multiple specific immune responses in the autologous host"; *Proc. Natl. Acad. Sci. U.S.A.*; Dec. 1995; pp. 11810-11813; vol. 92.

Shiku, Hiroshi er al.; "Development of a cancer vaccine: peptides, proteins, and DNA"; *Cancer Chemother. Pharmacol.*; 2000; pp. S77-S72; vol. 46 (Suppl.); Springer-Verlag.

Takeda, Junko et al.; "Anti-tumor immunity against CT26 colon tumor mice immunized with plasmid DNA encoding β-galactosidase fused to an envelope protein of endogenous retrovirus"; *Cellular Immunology*; 2000; pp. 11-18; vol. 204; Academic Press.

Velders, Markwin P. et al.; "Defined flanking spacers and enhanced proteolysis is essential for eradication of established tumors by an epitope string DNA vaccine"; *The Journal of Immunology*; 2001; pp. 5366-5373; vol. 166.

Chen, Y.T. et al.; 1997, *Proceedings of the National Academy of Sciences*, vol. 94, No. 5, pp. 1914-1918.

Jaeger, E., et al.; 2000, *Proceedings of the National Academy of Sciences*, vol. 97, No. 22, pp. 12198-12203.

Jaeger, E. et al.; 2001, Breast, pp. 158-160.

* cited by examiner

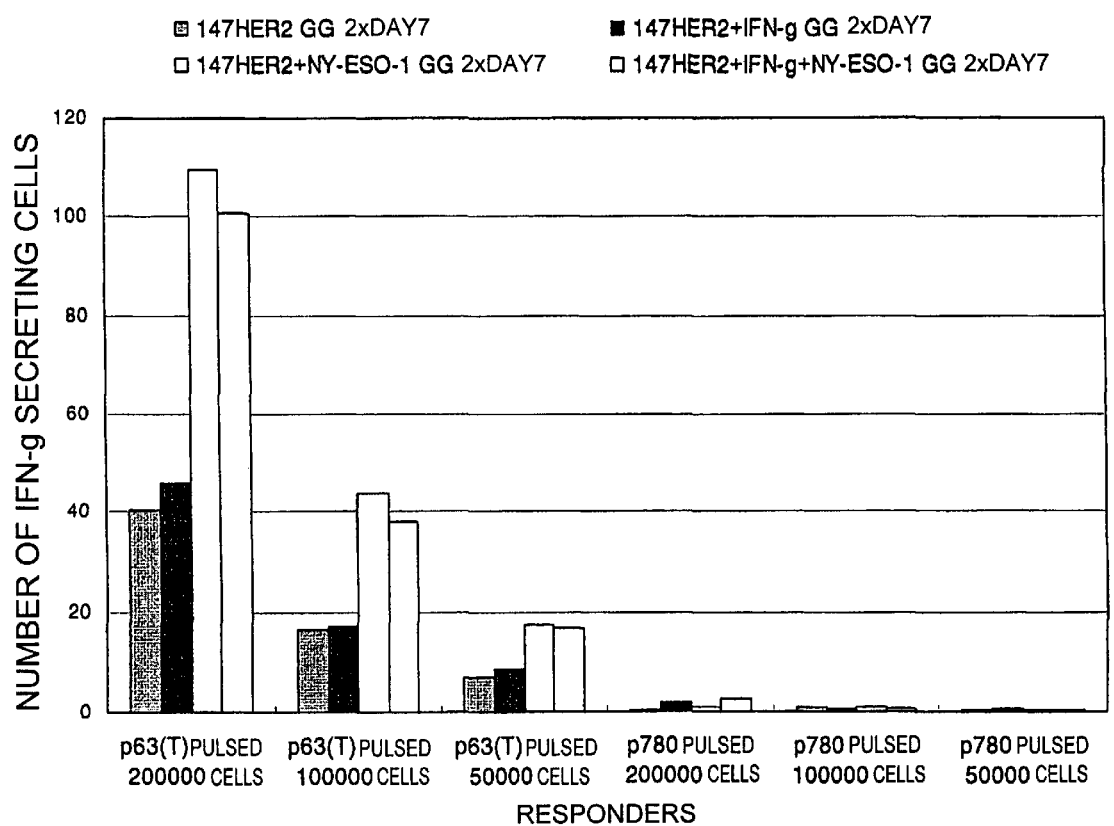

VACCINE COMPRISING A POLYNUCLEOTIDE ENCODING AN ANTIGEN RECOGNIZED BY A CD4+ HELPER T-CELL AND A POLYNUCLEOTIDE ENCODING A TUMOR SPECIFIC OR ASSOCIATED ANTIGEN RECOGNIZED BY A CD8+ CTL

CROSS-REFERENCES TO RELATED APPLICATIONS

This application is a continuation-in-part of PCT/JP02/05486, filed Jun. 4, 2002, which claims priority from Japanese Patent Application No. 2001-191334, filed Jun. 25, 2001 and has been published in non-English language. This application also claims priority from Japanese Patent Application No. 2002-372103, filed Dec. 24, 2002.

FIELD OF THE INVENTION

The present invention relates to a vaccine for developing tumor-specific immunity in vivo. Specifically, the invention relates to a polynucleotide vaccine comprising expression vectors encoding an antigen recognized by CD4+ helper T cells and an antigen recognized by CD8+ cytotoxic T cells (CTL). The antigen recognized by a CD4+ helper T cell is preferably a molecule detected via serological identification of antigen by recombinant cDNA expression cloning (SEREX) method. On the other hand, the antigen recognized by a CD8+ CTL preferably is a tumor-specific antigen, tumor-associated antigen or cell-associated antigen. Furthermore, so that the antigens recognized by CD4+ helper T cells and CD8+ CTL are expressed and presented on the same cell, the expression vectors are preferably immobilized on the same gold particle and administered into the cell by gene gun; however, the invention is not restricted thereto.

BACKGROUND OF THE INVENTION

For the past several years, cancer has been the leading cause of death in Japan. In addition to surgery, radiotherapy and chemotherapy, immunotherapy is the fourth option for cancer therapy. An in vivo system for immune response is utilized in immunotherapy. The immune response is elicited and controlled by the interaction amongst B lymphocytes, T lymphocytes, antibodies and antigen presenting cells (APC). First, an exogenous antigen is processed in the APC, and then it is presented in a form bound to the major histocompatibility complex (MHC) class 1 or class 2 to helper T cells. Upon the recognition by helper T cells of this exogenous antigen, T cells are activated and cytokines are secreted. The secreted cytokines help differentiation of antigen-stimulated B cells into antibody-forming cells and at the same time promote the differentiation of killer T cells. Finally, cells presenting antigens are eliminated by the secreted antibodies and by the activated killer T cells. This is how cellular and humoral responses operate in order to eliminate exogenous antigens.

The elimination process of antigen expressing cells by T cells can be broadly classified in three groups: 1) humoral immunity (activated helper T cell stimulates proliferation/differentiation of specific B cell clones, antibodies are produced and the antibodies recognize and eliminate antigens); 2) specific cellular immunity (activated helper T cells induce cytotoxic T cells (CTL) that react on specific antigens and the CTL directly reacts to the target); and 3) non-specific cellular immunity (activated helper T cells induce non-specific natural killer cells, activated macrophages, etc. and these cells function to eliminate antigens). As described above, T cells play a central role for recognizing target antigens to elicit immune response.

Regarding tumor rejection, antitumor immune responses in host cells have been known to be induced by appropriate immunization using syngeneic or self-derived tumor cells or fractions thereof (L. Gross, Cancer Res. 3: 326-333 (1943); E. J. Foley, Cancer Res. 13: 835-837 (1953); R. T. Prehn and J. M. Main, J. Natl. Cancer Inst. 18: 769-778 (1957); G. Klein et al., Cancer Res. 20: 1561-1572 (1980); L. Old et al., Ann. N.Y. Acad. Sci. 101: 80-106 (1962); A. Globerson and M. Feldman, J. Natl. Cancer Inst. 32: 1229-1243 (1964)). The role of CD8+ and CD4+ T cells in these tumor systems has been of enormous interest (R. J. North, Adv. Immunol. 35: 89-155 (1984); P. D. Greenberg, Adv. Immunol. 49: 281-355 (1991); D. M. Pardoll and S. L. Topalian, Curr. Opin. Immunol. 10: 588-594 (1998)). CD8+ T cells from specifically immunized mice are reported to be capable of destroying tumor target cells in vitro (H. Wagner et al., Adv. Cancer Res. 31: 77-124 (1980)). Furthermore, it has been reported that adoptive transfer of CD8+ T cells from immunized donors confers resistance to tumor transplants to naive mice (R. J. North, Adv. Immunol. 35: 89-155 (1984); P. D. Greenberg, Adv. Immunol. 49: 281-355 (1991); C. J. M. Melief, Adv. Cancer Res. 58: 143-175 (1992)). In addition, anti-CD8+ antibodies are known to abolish resistance to tumor transplantation in preimmunized mice (E. Nakayama and A. Uenaka, J. Exp. Med. 161: 345-355 (1985); X. G. Gu et al., Cancer Res., 58: 3385-3390 (1998); Y. Noguchi et al., Proc. Natl. Acad. Sci. USA 92: 2219-2223 (1994)). Over the past decade, MHC class I binding peptides derived from tumor cells of mice and human that are recognized by CD8+ T cells have been reported (T. Boon et al., Annu. Rev. Immunol. 12: 337-368 (1994); S. A. Rosenberg, Immunity 10: 281-287 (1999)).

Two forms exist for tumor antigens (target molecules on tumor cells). These are: (1) tumor peptide presented by MHC class I molecules, the target molecule of CD8+ CTL that is the leading character of cellular immunity; and (2) the target molecule of humoral immunity (antibody) that is expressed on the cell membrane of tumors is called tumor-associated antigen. Since a human tumor antigen recognized by a T cell has been defined at the genetic level, various human tumor rejection antigens have been discovered. Vaccination therapy is defined as a specific immunotherapy that uses a tumor rejection antigen and evident antitumor effect has been confirmed for the therapy. Furthermore, potentiation of immunotherapeutic effect by the combined use of cytokines and dendritic cells pulsed with antigenic peptides, or introduced with antigen genes has been attempted. Moreover, recently, DNA vaccines have been tested in the art.

A number of approaches to augment the helper action of CD4+ T cells have been attempted (D. Pardoll and S. L. Topalian, Curr. Opin. Immunol. 10: 588-594 (1998); R. F. Wang, Trends Immunol. 5: 269-276 (2001)). Earlier methods fall into one of three categories. One method involves modification of immunizing antigens itself. For example, haptenizing the antigen (Y. Mizushima et al., J. Natl. Cancer Inst. 74: 1269-1273 (1985)), linking heterologous immunogenic peptides directly onto the antigen (R. W. Chesnut et al., Vaccine Design, eds. M. F. Powell and M. J. Newman (Plenum, New York) 847-874 (1995); J. Rice et al., J. Immunol. 167: 1558-1565 (2001)), etc. The second is co-immunization with tumor antigens and molecules with strong helper determinants (R. Romieu et al., J. Immunol. 161: 5133-5137 (1998); N. Casares et al., Eur. J. Immunol. 31: 1780-1789 (2001)), such as viral vectors encoding tumor antigens (M. Wang et al., J. Immunol. 154: 4685-4692 (1995)). The third method utilizes molecular signals such as CD40 ligand (J. P. Ridge et al., Nature (London) 393: 474-478 (1998); S. R. M. Bennett et al., Nature (London) 393: 478-480 (1998); S. P. Schoenberg et al., Nature (London) 393: 480-483 (1998)) and other stimulatory/co-stimulatory signals (A. Porgador et al., J. Exp. Med. 188: 1075-1082 (1998)) involved in the helper function of CD4$^+$ T cells and in modulating the interaction of APCs with CD4$^+$ T cells. The discovery of such signals appears to provide methods to augment the response of CD8$^+$ T cells.

Antibodies have been generally relegated to a minor role in antitumor effector functions. However, tumor antigens like NY-ESO-1 elicits a strong integrated immune response involving both cellular and humoral immunities (Y.-T. Chen et al., Proc. Natl. Acad. Sci. USA 94: 1914-1918 (1997); E. Jager et al., J. Exp. Med. 187: 625-630 (2000); E. Jager et al., Proc. Natl. Acad. Sci. USA 97: 12198-12203 (2000)). Recently, M. Pfreundschuh and his colleagues developed a method called SEREX (Y.-T. Chen et al., Proc. Natl. Acad. Sci. USA 94: 1914-1918 (1997)) to identify tumor-associated antigens that may serve as vaccines against tumors. This method involves screening of cDNA expression libraries of human tumors with human sera. More than 1800 kinds of genes identified by SEREX are registered in the SEREX database on the internet (www.licr.org/SEREX.html).

However, there are still unsolved problems. Some of the problems include the kind of adjuvant or APC to be used for effectively inducing tumor-specific immunity with the identified antigenic peptides/DNAs to finally achieve complete recovery from tumor; or dealing with the escape of tumors from the immune system.

Helper T cells are often reported to be necessary for quantitative/qualitative amplification of CTL. However, the characteristics of antigen molecules recognized by these T cells and their functional impact on antitumor immune responses are still largely unknown (P. D. Greenberg, Adv. Immunol. 49: 281-355 (1991); D. M. Pardoll and S. L. Topalian, Curr. Opin. Immunol. 10: 588-594 (1998); S. R. Bennett et al., J. Exp. Med. 186: 65-70 (1997); R. F. Wang, Trends Immunol. 5: 269-276 (2001); C. Fayolle et al., J. Immunol. 147: 4069-4073 (1991); M. Shiral et al., J. Immunol. 152: 1549-1556 (1994); K. Hung et al., J. Exp. Med. 188: 2357-2368 (1998); F. Ossendorp et al., J. Exp. Med. 187: 693-702 (1998); Y. Shen and S. Fujimoto, Cancer Res. 56: 5005-5011 (1996); T. Nishimura et al., J. Exp. Med. 190: 617-627 (1999); D. R. Surman et al., J. Immunol. 164: 562-565 (2000); A. Franco et al., Nat. Immunol. 1: 145-150 (2000); C. N. Baxevanis et al., J. Immunol. 164: 3902-3912 (2000); F. Fallarino et al., J. Immunol. 165: 5495-5501 (2000); A. L. Marzo et al., Cancer Res. 59: 1071-3390 (1999); A. L. Marzo et al., J. Immunol. 165: 6047-6055 (2000)). The current hypothesis for serial intercellular interaction amongst helper T cells, CTLs and APCs points to the possibility that helper T cells related to antitumor immune response can recognize diverse antigens of a wide range (J. P. Ridge et al., Nature 393: 474-478 (1998); S. R. M. Bennett et al., Nature 393: 478-480 (1998); S. P. Schoenberger et al., Nature 393: 480-483 (1998); Z. Lu et al., J. Exp. Med. 191: 541-550 (2000)).

Great progress is being made in the analysis of humoral immune response in human and murine tumors by the above-described SEREX method (Y.-T. Chen et al., Proc. Natl. Acad. Sci. USA 94: 1914-1918 (1997); E. Jager et al., J. Exp. Med. 187: 625-630 (2000); E. Jager et al., Proc. Natl. Acad. Sci. USA 97: 12198-12203 (2000); U. Sahin et al., Proc. Natl. Acad. Sci. USA 92: 11810-11813 (1995); L. J. Old and Y.-T. Chen, J. Exp. Med. 187: 1163-1167 (1998); Y.-T. Chen, "Principle and Practice of the Biologic Therapy of Cancer", ed. S. A. Rosenberg (Lippincott Williams & Wilkins, Philadelphia) 557-570 (2000); T. Ono et al., Int. J. Cancer 88: 845-851 (2000)). Complete sequence determination of SEREX-defined genes show that many of them share the same sequence with the wild-type sequence, i.e., there are no amino acid substitutions included (L. J. Old and Y.-T. Chen, J. Exp. Med. 187: 1163-1167 (1998); Y.-T. Chen, "Principle and Practice of the Biologic Therapy of Cancer", ed. S. A. Rosenberg (Lippincott Williams & Wilkins, Philadelphia) 557-570 (2000)). Therefore, these molecules do not exhibit immunogenicity due to mutations. Furthermore, although some SEREX antigens show restricted tumor expression in normal tissues (e.g., cancer/testis antigens, melanocyte differentiation antigens, etc.), most of the SEREX-defined antigens are ubiquitously expressed. However, high-titered antibodies to these wild-type molecules are present more in serum samples of associated and non-associated cancer patients compared to normal healthy subjects. The current hypothesis is that amplified expression of these tumor products serves as the immunogenic stimulus for eliciting humoral immunity. Since all of these molecules are detected by antibodies of the IgG class, these wild-type molecules imply recognition by CD4$^+$ helper T cells. With regard to the above information, the present inventor examined in the present invention whether tumor-specific CD8$^+$ CTL can be amplified by activating CD4$^+$ helper T cells via immunogenic wild-type molecules of tumor cells. Namely, examined the involvement of the molecules in antitumor immune response.

DNA vaccines are demonstrated to induce both humoral and cellular immune responses upon intramuscular administration of naked DNA. The precise mechanism of induction of immune response by DNA vaccines is obscure (see, Pardoll et al., Immunity 3: 165-169 (1995)). However, its effectiveness is indicated by the induction of humoral and cellular immunities. This result indicates the expression of naked DNA following administration of a DNA vaccine, and that peptide products of the naked DNA are presented as antigens with both the MHC class I and class II proteins.

A T cell receptor on CTL recognizes an exogenous peptide derived from virus, bacteria, etc., bound to MHC class I and/or class II molecules as an antigen. Then, reactions such as production of various lymphokines and cell proliferation are known to be promoted to finally kill cells infected with the virus, bacteria, etc. Irrespective of their location in the original pathogen, these antigenic peptides are processed fragments that were intracellularly imported into APC or other cells. Known methods for artificial generation of CTL response include those using replication vectors that produce protein antigens in cells (J. R. Bennink and J. W. Yewdell, Curr. Top. Microbiol. Immunol. 163: 153 (1990); C. K. Stover et al., Nature 351: 456 (1991); A. Aldovini and R. A. Young, Nature 351: 479 (1991); R. Schfer et al., J. Immunol. 149: 53 (1992); C. S. Hahn et al., Proc. Natl. Acad. Sci. USA 89: 2679 (1992)) and methods wherein peptides are introduced into the cytosol (F. R. Carbone and M. J. Bevan, J. Exp. Med. 169: 603 (1989); K. Deres et al., Nature 342: 561 (1989); H. Takahashi et al., Nature 344: 873 (1990); D. S. Collins et al., J. Immunol. 148: 3336 (1992); M. J. Newman et al., J. Immunol. 148: 2357 (1992)).

Furthermore, a method for inoculating a vertebrate with naked polynucleotide as a vaccine has been discussed (WO90/11092 (Oct. 4, 1990)). Calcium chloride-precipitated DNA is known to be expressed via intravenous or intramuscular administration (N. Benvenisty and L. Reshef, Proc. Natl. Acad. Sci. USA 83: 9551-9555 (1986)). Moreover, in mice it was shown that DNA expression vector is incorporated into myocytes and expressed in the cell upon intramuscular injection of the vector (J. A. Wolff et al., Science 247:

1465 (1990); G. Ascadi et al., Nature 352: 815 (1991)). According to this method, the vector was sustained as an episome and did not replicate. However, permanent expression of the vector was observed following injection into the skeletal muscle of rat, fish and primate, as well as cardiac muscle of rat (H. Lin et al., Circulation 82: 2217 (1990); R. N. Kitsis et al., Proc. Natl. Acad. Sci. USA 88: 4138 (1991); E. Hansen et al., FEBS Lett. 290: 73 (1991); S. Jiao et al., Hum. Gene Therapy 3: 21 (1992); J. A. Wolff et al., Human Mol. Genet. 1: 363 (1992)). It was further reported that presentation of epitopes by B7 and MHC on the surface of APC play similar roles in the activation of CTL during tumor elimination (Edington, Biotechnology 11: 1117-1119 (1993)). When a MHC molecule on the surface of APC presents an epitope to a T cell receptor, a B7 expressed on the surface of the same APC binds to CTLA-4 or CD28 and functions as the second signal. As a result, CD4$^+$ helper T cells that emit signals for increasing APC destroying CD8$^+$ T cells rapidly proliferate.

For immunization with DNAs, the DNAs do not necessary have to be administered intramuscularly. For example, Tang et al. demonstrate that anti-bovine growth hormone (BGH) antibodies are produced in mice following administration of BGH-coated gold particles into the skin (Tang et al., Nature 356: 152-154 (1992)). Apart from skin, it is reported that muscular, adipose and mammary gland tissues of live animals can be transfected with DNAs (Furth et al., Analytical Biochemistry 205: 365-368 (1992)). Various methods for introducing nucleic acids are also reviewed (T. Friedman, Science 244: 1275-1281 (1989)). WO93/17706 describes a method of vaccine inoculation of an animal against a virus that comprises the steps of coating a carrier particle with a gene construct, and then administering the coated particle into a cell of the animal. Furthermore, DNA immunization against herpes virus (Cox et al., J. Virol. 67: 5664-5667 (1993)) has been reported. In addition, DNA vaccines and methods for producing and administering them are also described in U.S. Pat. No. 4,945,050, U.S. Pat. No. 5,589,466, and WO94/16737.

SUMMARY OF THE INVENTION

An objective of the present invention is to provide effective immunotherapy against tumors. Additional objectives include providing a radical treatment for early stage cancers, therapy for suppressing postoperative recurrence or metastasis of cancers, and treatment for patients detected to have inoperable tumors and for whom radical and chemical treatments were ineffective.

The present invention relates to a vaccine for eliciting tumor-specific immunity. The invention is based on the finding that tumor-specific immunity can be induced using an expression vector encoding an antigen recognized by CD4$^+$ T cells and an expression vector encoding an antigen recognized by CD8$^+$ T cells as a polynucleotide vaccine. Thus, the present invention relates to compositions comprising expression vectors encoding antigens recognized by CD4$^+$ T cells and CD8$^+$ T cells, respectively.

More specifically, the present invention relates to the following:

(1) a composition comprising an expression vector encoding (a) an antigen recognized by CD4$^+$ helper T cells, and (b) an antigen recognized by CD8$^+$ cytotoxic T cells;

(2) the composition of (1), wherein the antigen recognized by CD4$^+$ helper T cells is defined by the SEREX method;

(3) the composition of (1) or (2), wherein the antigen recognized by CD8$^+$ cytotoxic T cells is a tumor-specific antigen, tumor-associated antigen or cell-associated antigen;

(4) the composition of (2), wherein the antigen recognized by CD4$^+$ helper T cells is NY-ESO-1;

(5) the composition of (3), wherein the antigen recognized by CD8$^+$ cytotoxic T cells is HER2 or HER-2/neu;

(6) the composition of any one of (1) to (3), wherein the antigen recognized by CD4$^+$ helper T cells is Dna J-like 2 and that recognized by CD8$^+$ cytotoxic T cells is HER2 or HER2/neu;

(7) the composition of any one of (1) to (3), wherein the antigen recognized by CD4$^+$ helper T cells is NY-ESO-1 and that recognized by CD8$^+$ cytotoxic T cells is HER-2/neu;

(8) the composition of any one of (1) to (7), wherein the polynucleotides encoding respective antigens are contained in different expression vectors;

(9) the composition of (8), wherein both of the expression vectors are immobilized on the same carrier;

(10) a vaccine comprising any one of the compositions described in (1) to (9);

(11) the vaccine of (10), which is administered using a gene gun;

(12) the vaccine of (10) or (11), which is used for the therapy and/or prevention of cancer; and

(13) a method for inducing tumor-specific immunity in a mammal, comprising the step of administering the composition of any one of (1) to (9) to the mammal.

BRIEF DESCRIPTION OF THE DRAWINGS

FIG. 1, panel b shows the results when human SEREX-defined molecules were used.

FIG. 6 depicts a graph showing the result of ELISPOT assay using 147HER2, p63(T) mini gene, NY-ESO-1 and mmIFN-γ.

DETAILED DESCRIPTION OF THE INVENTION

Figure 1:
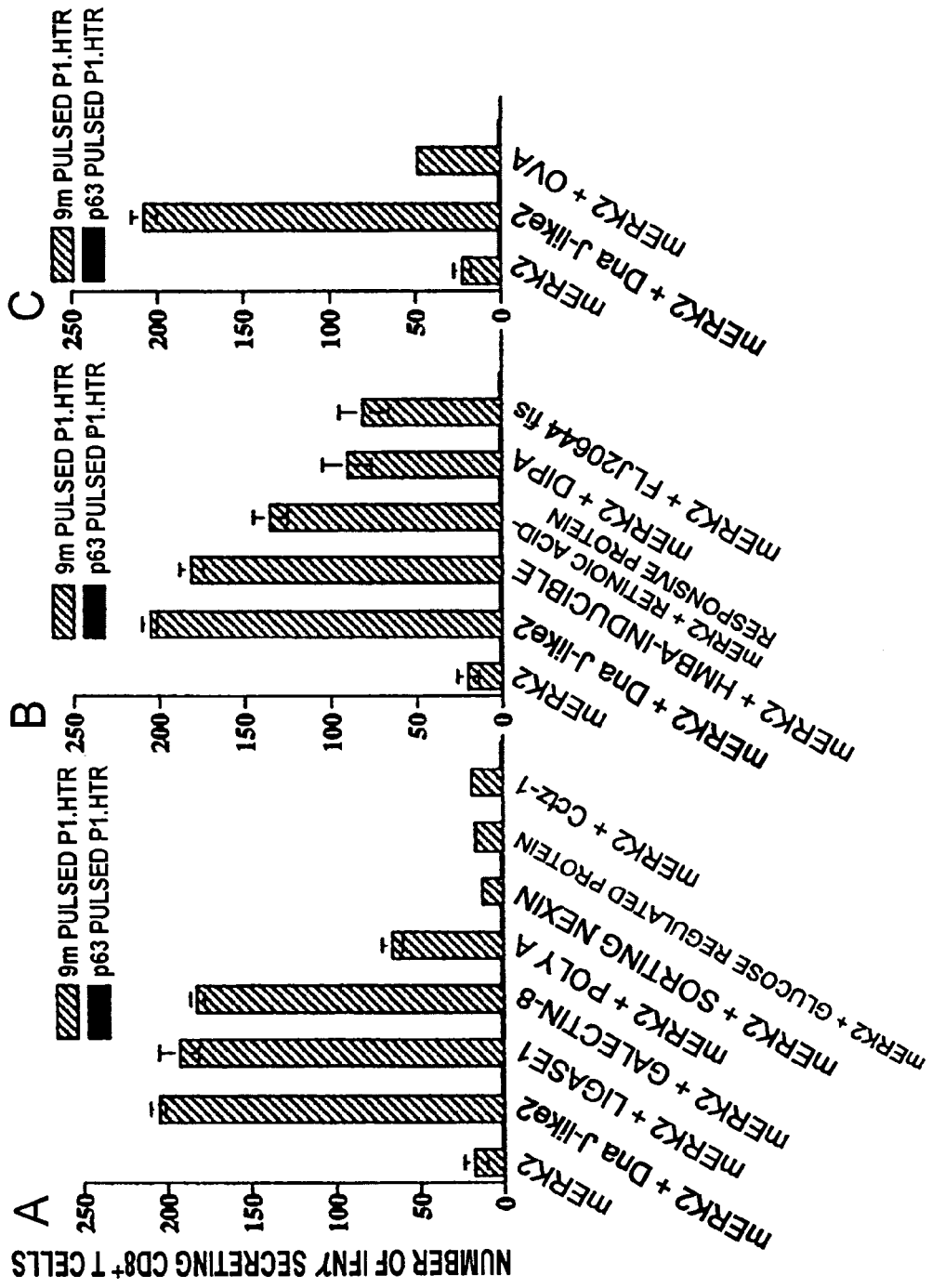
FIG. 1 depicts graphs showing the increase in the number of 9m peptide specific CD 8$^+$ T cells that are generated by the immunization using mERK2 and SEREX-defined molecules.

The words "a", "an" and "the" as used herein mean "at least one" unless otherwise specifically indicated.

The present invention relates to a vaccine for eliciting tumor-specific immunity. The invention is based on the finding that tumor-specific immunity can be induced using an expression vector encoding an antigen recognized by CD4$^+$ T cells and an expression vector encoding an antigen recognized by CD8$^+$ T cells as a polynucleotide vaccine. Thus, the present invention relates to compositions comprising expression vectors encoding antigens recognized by CD4$^+$ T cells and CD8$^+$ T cells, respectively. Specifically, the antigen recognized by CD4$^+$ helper T cells is a molecule determined by the SEREX method, and that recognized by CD8$^+$ CTL is a tumor-specific antigen, tumor-associated antigen or cell-associated antigen. Furthermore, the antigens recognized by CD4+ helper T cells and CD8+ CTL are immobilized on the same carrier particle and administered into a cell to express and present them on the same cell; however, the invention is not restricted thereto.

As described herein, the phrase "antigen recognized by CD4+ helper T cells" refers to a polypeptide that comprises a portion that serves as an epitope of a glycoprotein expressed on mature helper T cell or precursor cell thereof. When a T cell receptor recognizes an antigen presented by MHC class II, CD4 binds to the MHC class II β2 domain and thus enhances the ability of the T cell to recognize antigens. CD4 further transmits signal into the cell, and functions as a molecule to promote proliferation and secretion of cytokines. According to the present invention, molecules identified by SEREX are particularly preferred among the molecules recognized by CD4+ helper T cells. Such molecules include heat shock protein Dna J-like 2, DNA ligase 1, galectin 1, poly(A) binding protein, $Homo$ $sapiens$ hexamethylene-bis-acetamide-inducible (XM_008348), human retinoic acid-responsive protein (U50383), $H.$ $sapiens$ hepatitis delta antigen interacting protein A (DIPA)(XM_006503), $H.$ $sapiens$ cDNA FLJ20644 fis clone KAT002588 (FLJ20644fis) (AK000651), fetal antigen NY-ESO-1, etc.; but are not restricted thereto. The phrase "SEREX-defined molecule" herein refers to such molecules identified by SEREX. In addition, the phrase "immunogenic wild-type cellular molecule" herein refers specifically to the molecules identified by SEREX that are recognized by CD4+ helper T cells as described above. Most of the molecules identified by SEREX are wild-type molecules generally expressed in normal healthy people. To avoid occurrence of inutile immune response on healthy tissues it is preferable to select SEREX-defined molecules that are restrictedly expressed on tumors as the antigen recognized by CD4+ helper T cells of the present invention. Such molecules include antigens such as NY-ESO-1 which is expressed in cancer tissues and testis. The use of NY-ESO-1 is particularly preferable in the present invention.

Furthermore, herein, the phrase "antigen recognized by CD8+ cytotoxic T cells (CTL)" refers to polypeptides comprising a portion that serves as an epitope of transmembrane glycoprotein CD8 expressed on CTL and precursor cells thereof. When a T cell receptor recognizes an antigen presented by MHC class I, it binds to the α3 domain of MHC class I. The antigen recognizing ability of the T cell is enhanced by the binding and the signal is transmitted into the cell. The "antigen recognized by CD8+ cytotoxic T cells" is a molecule having the function to enhance the proliferation and cytotoxic activity of the T cell via such pathways. Particularly preferred molecules include tumor-specific antigens, tumor-associated antigens and cell-associated antigens. The phrase "tumor-specific antigens, tumor-associated antigens and cell-associated antigens" refer to antigens that are related to tumors or antigens specifically expressed on specific tumor cells. Exemplary antigens include those whose expression is limited to cancer and testis, such as MAGE, BAGE, GAGE and NY-ESO-1; cancer-specific mutant antigen derived from gene products that were mutated during the process of carcinogenesis, such as CDK4, MUM-1, CASP-8, ras and bcr-abl; tissue specific antigens whose expression is limited to specific tissues, such as MART-1, TRP, tyrosinase, gp100, PSA, proteinase 3; protein antigens highly expressed in cancers, such as HER2/neu, CEA, SARTI; and viral antigens, such as EBV, HPV and HTLV-1. The antigen recognized by CD8+ cytotoxic T cells (CTL) of the present invention may be the full length of and of these antigens, but may also be fragments thereof comprising peptides that may be presented by binding to a MHC class I molecule and reacts with the CTL.

These molecules further include polypeptides such as mutant MAP kinase ERK2 (mERK2) and HER2. HER2 is a tumor rejection antigen of congenital sarcoma CMS17HER2, a cell line derived from CMS5a generated by transfection with human HER2 cDNA (c-erb-2/HER2/neu cDNA)(Y. Nagata et al., J. Immunol. 159: 1336-1343 (1997); X. Gu et al., Cancer Res. 58: 3385-3390 (1998); Y. Ikuta et al., Int. J. Cancer 87: 553-558 (2000); T. Okugawa et al., Eur. J. Immunol. 30: 3338-3346 (2000)). The HER2 is preferred as the antigen recognized by CD8+ cytotoxic T cells (CTL). The full-length sequence or immunogenic fragments of the HER2 may be used in the present invention. A 9mer peptide, HER2 p63-71(T) peptide (amino acid sequence "TYLPTNASL") has been identified as a tumor rejection antigen against CMS17HER2 or as the target of CD8+ $K^d$-restricted cytotoxic T cells (Y. Nagata et al., J. Immunol. 159: 1336-1343 (1997); X. Gu et al., Cancer Res. 58: 3385-3390 (1998); Y. Ikuta et al., Int. J. Cancer 87: 553-558 (2000); T. Okugawa et al., Eur. J. Immunol. 30: 3338-3346 (2000)). Fragments comprising such antigenic sites are particularly preferred.

Furthermore, the combination of HER2 and Dna J-like 2 is particularly preferred as the antigens of the present invention. NY-ESO-1 is a fetal antigen and thus its expression is restricted to cancer patients in adults. Therefore NY-ESO-1 is particularly preferred as the antigen recognized by CD4+ helper T cells in the present invention. The most preferable combination of the present invention is NY-ESO-1 and HER-2/neu as the antigen recognized by CD8+ cytotoxic T cells. The sequence of NY-ESO-1 and HER-2/neu can be found in database (GenBank Accession Nos. AJ003149 and NM004448, respectively).

Polynucleotides encoding the antigens of the present invention are not restricted and may be DNA, RNA, etc., as long as they can elicit the desired immune response by administering them to the host animal according to the method of the present invention. The polynucleotides encoding antigens of the present invention may be those whose nucleotide sequence is artificially modified by one or more amino acids deletions, substitutions, insertions and/or additions according to known methods such as site directed mutagenesis (see, edited by Ausubel et al., Current Protocols in Molecular Biology, John Wiley & Sons, Section 8.1-8.5 (1987)) as long as the polypeptide encoded by the polynucleotide can generate desired immune response in the host. Furthermore, as long as it can elicit a desired immune response in the host, the polynucleotide may encode polypeptides having mutations that exist in nature. Such mutants existing in nature may be isolated utilizing known hybridization techniques (see, edit. Ausubel et al., Current Protocols in Molecular Biology, John Wiley & Sons, Section 6.3-6.4 (1987)) and gene amplification techniques (PCR)(see, edit. Ausubel et al., Current Protocols in Molecular Biology, John Wiley & Sons, Section 6.1-6.4 (1987)).

Moreover, if a gene encoding an antigenic protein is known, one skilled in the art can readily analyze hydrophobic and/or hydrophilic regions within the amino acid sequence of the protein (Kyte and Doolittle, J. Mol. Biol. 157: 105-122 (1982)), analyze its secondary structure (Chou and Fasman, Ann. Rev. Biochem. 47: 251-276 (1978)), and synthesize peptides with the predicted amino acid sequence to determine its antigenicity by PEPSCAN (Nature 314 (1985); Published Japanese Translation of International Publication No. Sho 60-500684), etc. Thus, a polynucleotide encoding a peptide fragment that comprises the epitope site determined base on the above-described method may be prepared by chemical synthesis and so on, to be used as the antigen of the present invention in an expression vector.

The expression vector used in the present invention is a recombinant vector wherein the antigen gene of the present invention is inserted therein. The vectors to insert the antigen gene include plasmids, phages, cosmids, viruses, and other conventional vectors in the technical field of the present invention. Those skilled in the art can construct various plasmids and vectors based on well known techniques (edited by Sambrook et al. Molecular Cloning: A Laboratory Manual (Cold Spring Harbor Laboratory, N.Y. (1989) and edited by Ausubel et al., Current Protocols in Molecular Biology, John Wiley & Sons, Section 6.1-6.4 (1987)).

Herein, factors such as promoter and terminator regulating the expression in the host can be appropriately selected by those skilled in the art from known regulatory sequences depending upon the specific type of host and object, and desired arrangement (i.e., upstream and/or downstream to the antigen gene). Therefore, regulatory sequences derived from the antigen or heterogeneous regulatory sequences may be used in the present invention. Furthermore, if needed, markers such as an antibiotic resistance marker may be used as the expression vector in the present invention. Commercially available multiple vectors may be used. However, it is preferred to delete nonessential polynucleotide sequences from the vector in the present invention. In addition, the polynucleotide encoding an antigen recognized by $CD4^+$ helper T cells and that encoding an antigen recognized by $CD8^+$ CTL used in the present invention may be included in different expression vectors or constructed to be expressed from a single vector as long as they can be controlled for their expression on the same cell.

Upon introduction into the tissue of an animal, the vaccine of the present invention induces in vivo expression of the present antigen and elicits the desired immune response. Various methods are known for introducing nucleic acids in vivo (T. Friedman, Science 244: 1275-1281 (1989)). Any method may be used as long as the antigens of the present inventions are expressed in vivo and elicit the desired immune response.

The compositions of the present invention are useful as vaccines and can be used as naked plasmids. They may be packaged into a liposome, formed as various virus vectors including retrovirus vectors, adenovirus vectors, vacciniavirus vectors, poxvirus vectors, adeno-associated virus vectors and HVJ (hemmagglutinating virus of Japan) vectors (see, e.g., K. Adolph "Virus genomic methods", CRC Press, Florida (1996)), or coated on beads (carriers) such as colloidal gold particles. Preferably, the vectors expressing the antigens recognized by $CD4^+$ helper T cells and $CD8^+$ CTL, respectively, are in the form adhered to a carrier particle, such as gold particle, for introduction into the body by gene gun, etc.; however, the present invention is not limited thereto. Methods for coating polynucleotides on a carrier particle are known in the art (see, for example, WO93/17706). Finally, the polynucleotides are prepared in a solution such as physiological saline adapted for in vivo administration. The composition of the present invention may be used as a vaccine, in combination with adjuvants such as proteins or other carriers that are known in the art for enhancing immune reactions. Moreover, agents such as calcium ion that help the intracellular uptake of plasmids may be used in combination. In addition, pharmaceutically accepted agents that achieve easier transfection may be combined as required.

The polynucleotide vaccine of the present invention may be administered by any method as long as it generates an immune response within the host animal. Preferably, the composition of the present invention is administered at a dose sufficient to induce immune response in the host animal by appropriate methods including injections, infusion or gas-induced particle bombardment method (using gene gun, etc.) via parenteral routes, such as intravenous, intraperitoneal, subcutaneous, intradermal, via adipose tissue, via mammary gland tissue, inhalation or intramuscular, or mucosal routes in the form of nose drops. Furthermore, a host animal may be immunized by administering the present composition into a blood cell, bone marrow-derived cell (e.g., APC) etc. by ex vivo liposome transfection, particle bombardment method, virus infection, etc., and then reintroducing the cell into the animal. Among the above-mentioned administration methods, the gene transformation method using accelerated particles is described in U.S. Pat. No. 4,945,050 and devices base on modified methods thereof are commercially available (BioRad Laboratories).

The specific type of host animal of the present invention is not limited as long as the tumor immune response of the animal is enhanced by the composition of the present invention. Specific examples include mammals, such as mice, rats, bovines, pigs, primates like monkey and human, etc. Preferable host animals of the present invention include primates, particularly human.

The dose of the composition of the present invention depends on the immunogenicity in the host of the ingredient comprises in the composition. However, those skilled in the art can determine appropriate dose required for immunization by administering a determined dose of the composition into a test animal and measuring the antibody titer by assay methods such as ELISA, detecting CTL response by measurement of chromium release, etc., or observing immune response by detecting Th response using cytokine release measurement. Those skilled in the art will recognize that the immunogenicity of the ingredient in the composition depends also on the intensity of the regulatory sequence, such as transcription and translation promoters, used in the expression vector of the present invention. Furthermore, those skilled in the art can readily adjust the dose of the composition of the present invention based on the specific expression vector used.

As described above, the present invention revealed the critical role of $CD4^+$ T cells in tumor-specific immune response by $CD8^+$ T cells against immunogenic wild-type cellular molecules. A phenomenon similar to the $CD8^+$ T cell immune response against tumor antigen heightened by co-recognition of SEREX-defined antigen in mice appears to exist in human. The heightened immune response results from the simultaneous incorporation by APC of complex antigenic mixture of destructed tumor cells. The resistance to tumor challenge increases in mice co-immunized with SEREX antigen and tumor-specific antigen, tumor-associated antigen or cell-associated antigen. This approach is an attractive strategy for cancer immunotherapy in humans and one that will be facilitated by the extensive base of information about SEREX-defined humor tumor antigens.

The vaccine of the present invention for eliciting tumor-specific immunity provides an effective immunotherapy method against tumors. The vaccine of the present invention shows both preventive and therapeutic effects. Thus, it is expected to provide a radical treatment for early stage cancers, therapy for suppressing postoperative recurrence or metastasis of cancers, and treatment for patients detected to have tumor but who cannot be operated and for whom radical and chemical treatments were found ineffective.

Hereinafter, the present invention is described in detail below with reference to Examples. However, it should not be construed as being limited thereto.

EXAMPLE 1

Identification of Tumor-derived Immunogenic Molecules

To identify immunogenic molecules in murine tumor cells, cDNA λ phage libraries prepared from BALB/c origin 3-methylchoranthrene-induced sarcoma CMS5, CMS2, CMS8 and CMS13 lines (A. B. DeLeo et al., J. Exp. Med. 146: 720-734 (1977)), and CMS5a and CMS5 m subcloned from CMS5 were screened by SEREX (U. Sahin et al., Proc. Natl. Acad. Sci. USA 92: 11810-11813 (1995)) using sera samples (IgG antibody) from syngeneic mice bearing cognate tumor lines. Among the array of genes detected, four of the most frequently detected gene products were Mus heat shock protein Dna J-like 2 (AF055664), Mus galectin-8 (hereinafter referred to as galecting-8)(AF218069), Mus DNA ligase 1 (U19604) and Mus poly(A) binding protein cytoplasmic 1 (hereinafter referred to as poly(A))(X65553). Analyses of the coding sequences of these genes did not reveal any mutations as compared to registered sequences in GenBank (Table 1). These highly immunogenic tumor antigens were selected for further study. In addition, three cDNAs that were consistently negative in repetitive SEREX screenings, Mus sorting nexin 1(AB019214), Mus glucose-regulated protein (D78645) and Mus Cctz-1 gene for chaperon containing TCP-1-zeta-1 subunit (AB022159) were included to represent nonimmunogenic molecules derived from tumor cells.

Furthermore, immunogenic molecules were detected with serum of idiopathic thrombocytopenic purpura patients using cDNAs encoding antigens of UT-7/TPO (human megakaryoblastic leukemia cell line) (N. Komatsu et al., Blood 87: 4552-4560 (1996)). For further study, (1) *Homo sapiens* hexamethylene-bis-acetamide-inducible (XM_008348), (2) human retinoic acid-responsive protein (U50383), (3) *H. sapiens* hepatitis delta antigen interacting protein A (DIPA) (XM_006503) and (4) *H. sapiens* cDNA FLJ20644 fis clone KATO2588 (FLJ20644fis)(AK000651) were selected as SELEX-defined human genes.

TABLE 1

| Antigens(accession number) | Size (bp) | Source (cDNA expression libraries) |
|---|---|---|
| Murine molecules Immunogenic* | | |
| heat shock protein, Dna J-like 2 (AF55664) | 2,242 | CMS5a and CMS2 |
| DNA ligase 1 (U19604) | 3,172 | CMS13 |
| galectin-8 | 1,086 | CMS2 and CMS7 |
| poly(A) binding protein, cytoplasmic 1 (X65553) | 2,244 | CMS8 |
| Nonimmunogenic** | | |
| sorting nexin 1 (AB019214) | 2,007 | CMS5a |
| glucose-regulated protein (D78645) | 2,408 | CMS5a |
| Cctz-1 gene for chaperon containing TCP-1-zeta-1 subunit (AB022159) | 19,505 | CMS5a |
| Human molecules Immunogenic*** | | |
| *Homo sapiens* HMBA-inducible (XM_008348) | 3,594 | UT-7/TPO |
| human retinoic acid-responsive protein (U50383) | 2,520 | UT-7/TPO |
| *H.sapiens* hepatitis delta antigen protein A (XM_006503) | 997 | UT-7/TPO |
| *H.sapiens* cDNA FLJ20644 fis, clone KATO02588 (AK000651) | 1,781 | UT-7/TPO |

HMBA; hexamethylene-bis-acetamide
*Detected by syngeneic antibody from tumor-bearing mice in SEREX analysis of cDNA expression libraries of the corresponding tumor.
**Obtained by random selection of clones from the CMS5a cDNA expression library.
***Detected by antibody from patients with idiopathic thrombocytopenic purpura in SEREX analysis of cDNA expression libraries of the human megakaryoblastic leukemia cell line.

EXAMPLE 2

Enhancement of Tumor-specific CD8$^+$ T Cell Production by SEREX-Defined Immunogenic Wild-type Cellular Molecules cDNA encoding the whole protein of mERK2 was digested with EcoR I and BamH I, and then cloned into the EcoR I and BamH I site of pCAGGS-New (H. Niwa et al., Gene 106: 193-200 (1991)). The mERK2 plasmid was maintained in DH5α (TOYOBO, Osaka, Japan) and purified using QIAGEN Endfree Mega kit (QIAGEN, Hilden, Germany). 1 µg of any of following (1) to (4) were mixed with 0.5 mg of 1 µm gold particles (BioRad, Hercules, Calif.): (1) said mERK2 plasmid alone; (2) a mixture of said mERK2 plasmid and plasmid encoding either murine SEREX-defined molecules selected from the group of Dna J-like 2, DNA ligase 1, galectin-8 and poly(A), or human SEREX-defined molecules selected from the group of hexamethylene-bis-acetamide (HMBA)-inducible, retinoic acid-responsive protein, delta antigen interacting protein A (DIPA) and FLJ20644fis; (3) a mixture of said mERK2 plasmid and plasmid encoding a molecule that was negative in SEREX (sorting nexin, glucose-regulated protein or Cctz-1); and (4) a mixture of said mERK2 plasmid and plasmid encoding chicken ovalbumin. The mixture was added to a centrifugate tube containing appropriate amount of 0.05 M spermidine (Nacalai Tesque, Kyoto, Japan) to adhere the plasmid DNAs to the gold particles (see, C. Condon et al., Nat. Med. 2: 1122-1128 (1997); A. Porgador et al., J. Exp. Med. 188: 1075-1082 (1998); D. Klinman et al., J. Immunol. 160: 2388-2392 (1998); C. A. T. Torres et al., J. Immunol. 158: 4529-4532 (1997); A. Iwasaki et al., J. Immunol. 159: 11-14 (1997)). The immunization of seven to nine week old BALB/c mice was performed by abdominal delivery of the plasmid-coated gold particles using Helios Gene Gun System (BioRad, Hercules, Calif.) at a helium discharge pressure of 350-400 psi. Mice received a booster injection 2 weeks after the initial immunization. A week later, CD8$^+$ T cells were purified from the spleen of the mice.

Peptide 9m is a 9-mer peptide (amino acid sequence "QYIHSANVL") identified as an antigenic peptide specific for CMS5, a 3-methylchloranthrene-induced murine sarcoma, and was indicated as a tumor rejection antigen of CMS5 sarcoma (see, H. Ikeda et al., Proc. Natl. Acad. Sci. USA 94: 6375-6379 (1997)). The production of the peptide 9m was ordered to TaKaRa (Otsu, Japan). Furthermore, to confirm the specificity of enzyme-linked immunospot assay, tumor rejection antigen against CMS17HER2, or HER2 p63-71(T) peptide was used as a control. HER2 p63-71(T) peptide is a 9-mer peptide identified as the target of CD8$^+$ K$^d$ restricted cytotoxic T cell (amino acid sequence "TYLPT-NASL"; see Y. Nagata et al., J. Immunol. 159: 1336-1343 (1997); X. Gu et al., Cancer Res. 58: 3385-3390 (1998); Y. Ikuta et al., Int. J. Cancer 87: 553-558 (2000); T. Okugawa et al., Eur. J. Immunol. 30: 3338-3346 (2000); similar to 9m, ordered for production to TaKaRa)(hereinafter referred to as p63).

The 9m peptide was applied to P1.HTR, a mastocytoma cell line of DBA/2 origin (A. Van Pel et al., Somatic Cell. Genet. 11: 467-475 (1985)).

Cells secreting IFNγ among the above-described CD8+ T cell obtained from mice spleen were detected by ELISPOT assay using the P1.HTR cell stimulated with 9m peptide or p63-71 (T). Thus, the existence of CD8+ cells specific to 9m peptide was assessed quantitatively.

By modifying the method of Power et al. (Power et al., J. Immunol. Methods 227: 99-107 (1999)), ELISPOT assay was performed as follows. First, rat anti-murine INFα antibody (clone R 4-6A2; Pharmingen, SanDiego, Calif.) was incubated at 4° C. overnight in a nitrocellulose-coated 96-well microtiter plate (Millipore, Bedford, Mass.). After washing, the antibody was blocked at 37° C. for 1 to 2 hours. $1 \times 10^6$ CD8+ T cells or $1 \times 10^6$ P 1.HTR were added to each well, incubated at 37° C. for 24 hours and the wells were washed thoroughly. Then, biotinylated anti-murine IFNγ antibody (clone XMG1.2; Pharmingen, SanDiego, Calif.) was added and further incubated at 4° C. overnight. After washing the wells, alkaline phosphatase-bound streptoavidine (MABTECH, Nacka, Sweden) was added and incubated at room temperature for 1.5 hours. Spots were generated by the addition of alkaline phosphatase-bound substrate kit (Bio-Rad, Hercules, Calif.). The plate was thoroughly washed, dried and the number of formed spots counted using a dissecting microscope and Axloplan2 imaging system (Carl Zeiss vision, Hailbergmoss, Germany).

Figure 2:
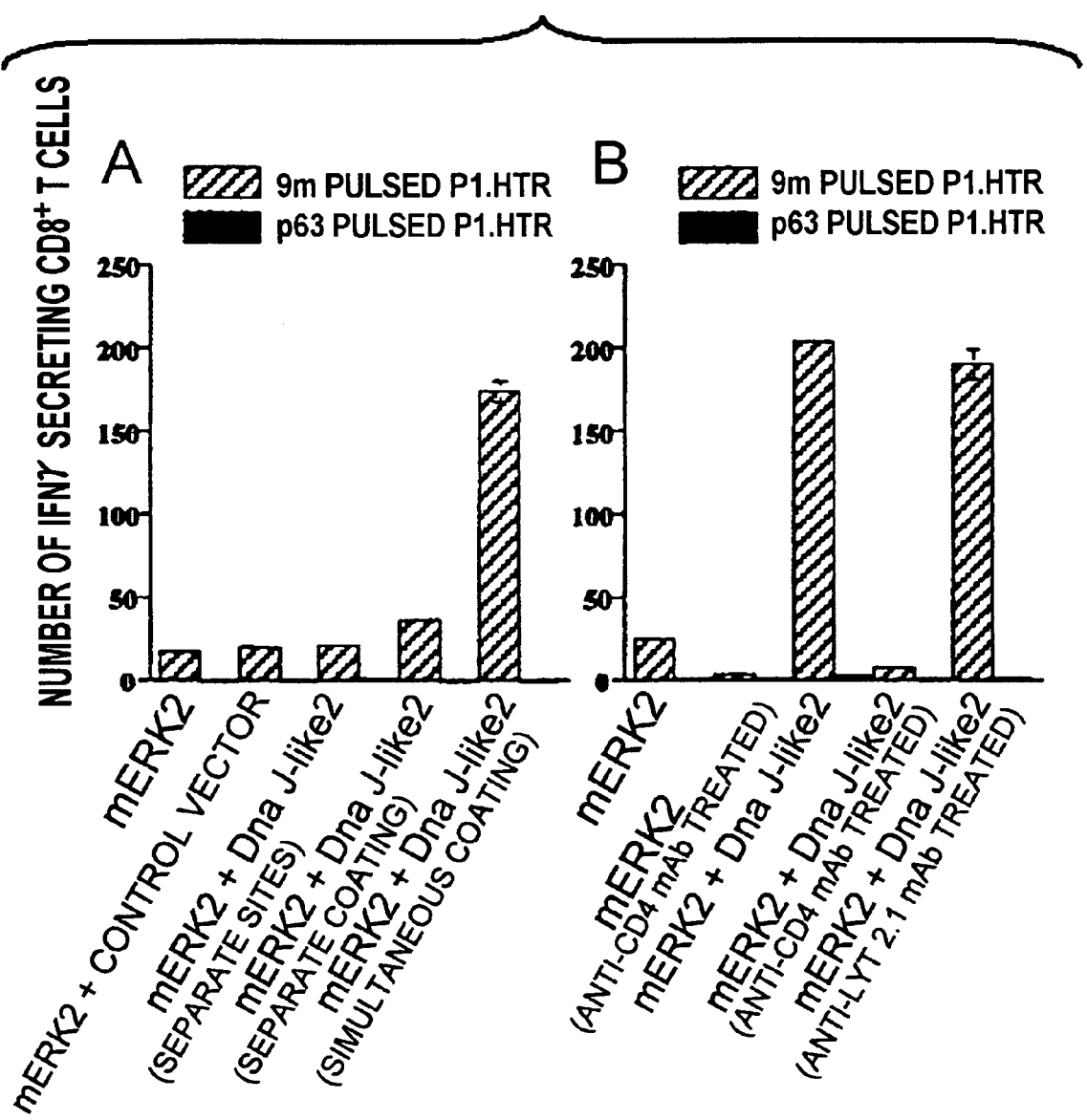
FIG. 2 depicts graphs showing that the enhancement of 9m peptide-specific CD8$^+$ T cells induced by SEREX-defined molecules requires co-presentation of 9m peptide (panel a) and existence of CD4$^+$ T cells (panel b).

As a result, mice immunized with mERK2 cDNA alone generated low levels of 9m peptide-specific CD8+ T cells (FIG. 1). On the other hand, mice immunized with mERK2 and SEREX-defined antigens showed a striking increase in the number of 9m peptide-specific CD8+ T cells (FIG. 1, panel a). The number of positive spots in these mice was three to 10 times higher than in mice immunized with mERK2 cDNA alone. In contrast, immunization with mErk2 plasmid mixed with a plasmid encoding a molecule that was not detected in the repeated SEREX analyses (e.g., sorting nexin, glucose-regulated protein or Cctz-1) showed no increase of 9m peptide specific CD8+ T cells (FIG. 1 panel a). Co-immunization with the control vector did not increase the number of 9m peptide specific CD8+ T cells (FIG. 2, panel a). There were remarkably few number of spots detected in the p63-applied target cells. Thus, the specificity of the present ELISPOT assay was confirmed.

The cDNA encoding human SEREX-defined immunogenic heterologous molecules also greatly increased 9m peptide specific CD8+ T cell responses when presented together with mERK2 (FIG. 1, panel b). In contrast, co-immunization with chicken ovalbumin resulted only in a marginal increase in specific CD8+ T cell reactivity (FIG. 1, panel c).

In FIG. 1, each bar represents the number of IFNγ-secreting CD8+ T cells per $10^5$ CD8 T cells (FIG. 1, panel a). Target cells were 9m-pulsed P1.HTR (hatched bars) or p63-pulsed P1.HTR (solid bars) as a control. Data are indicated as mean ±SEM of three experiments.

EXAMPLE 3

Confirmation on the Requirement of the Co-presentation of SEREX-defined Molecules and CD8+ T Cell Epitopes for Enhancing CD8+ T Cell Response To determine whether the CD8+ T cell epitopes and SEREX-defined molecules need to be co-presented on the same gold particle, mice were immunized by either of the following methods:

(1) immunization using a mixture of gold particles coated with mERK2 plasmid alone and gold particles coated with Dna J-like 2 plasmid alone (individually coated); or (2) injection of particles coated with mERK2 plasmid alone and particles coated with Dna J-like 2 plasmid alone on opposite sides of the abdomen (different sites).

The production of gold particles coated with plasmids and immunization were performed similar to the method as described in Example 2. Moreover, the same target cells were used. Then, the number of 9m peptide-specific CD8+ T cells were counted.

Increase in the number of 9m peptide-specific CD8+ T cells was observed only in animals immunized with particles that were coated with both the plasmid encoding the antigen recognized by CD4+ T cells and plasmid encoding the antigen recognized by CD8+ T cells. No increase in CD8+ T cells specific for 9m peptides was observed in either of the above-described (1) or (2) (FIG. 2, panel a). Thus, CD4+ T cells were confirmed to recognize SEREX-defined antigenic peptides presented by cells that also present a 9m T cell epitope derived from mERK2. Data are represented by mean ±SEM of three experiments.

EXAMPLE 4

CD4+ T Cell Dependence of Enhanced CD8+ T Cell Response

The present inventor examined whether CD4+ T cells were involved in promoting induction of 9m peptide-specific CD8+ T cells by SEREX-defined antigens. BALB/c mice were treated with anti-CD4 antibody (GK1.5) or anti-Lyt2.1 antibody as a control. Then, as described in Example 2, mice treated with either of the aforementioned antibodies were immunized with mERK2 plasmid and Dna J-like 2 plasmid. The same target cell as in Example 2 was used for this experiment.

When mice were treated with anti-CD4 antibody (GK1.5) before the immunization with the mixture of plasmid encoding mERK2 and plasmid encoding the SEREX-defined antigen Dna J-like 2, there was no increase in 9m peptide-specific CD8+ T cells. However, the control antibody (Lyt-2.1) did not inhibit the increase of 9m peptide-specific CD8+ T cells (FIG. 2, panel b). Thus, the increase of CD8+ T cells due to immunization with mERK2 plasmid and Dna J-like 2 plasmid was shown to depend on CD4+ T cells. Data are represented by mean ±SEM of three experiments.

EXAMPLE 5

Figure 3:
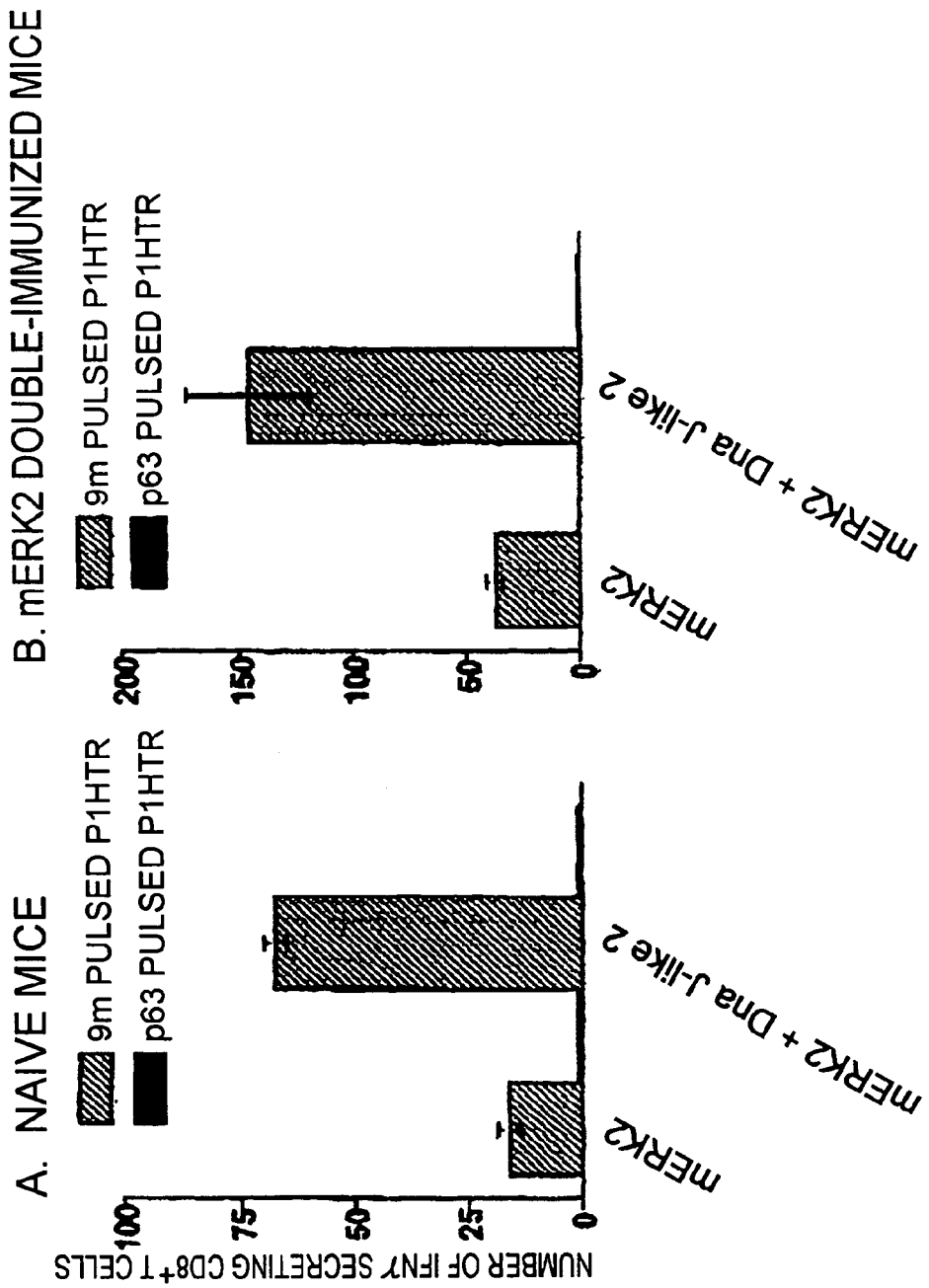
FIG. 3 depicts graphs showing that the helper activity due to CD4$^+$ T cells recognizing SEREX-defined antigen molecules enhances 9m-specific CD8$^+$ T cells in both the primary and secondary responses.

Relation of Immunogenic Helper Wild-type Cellular Molecules on Primary and Secondary Tumor-specific Responses of CD8+ T Cells Naive mice (FIG. 3, panel a) and mice that were twice preimmunized with plasmid encoding mERK2 (FIG. 3, panel b) were used as models for primary and secondary responses, respectively. According to the method described in Example 2, mice were immunized with plasmid coding mERK2 or plasmids encoding mERK2 and Dna J-like 2. 14 days after the immunization, mice were similarly analyzed for 9m-specific CD8$^+$ T cells. The results are shown in FIG. 3. Data are represented by mean ±SEM of three experiments. In both the models, the mice immunized with the plasmid encoding mERK2 alone, the number of 9m-specific CD8$^+$ T cells significantly increased in mice immunized with plasmids encoding mERK2 and Dna J-like 2.

EXAMPLE 6

Figure 4:
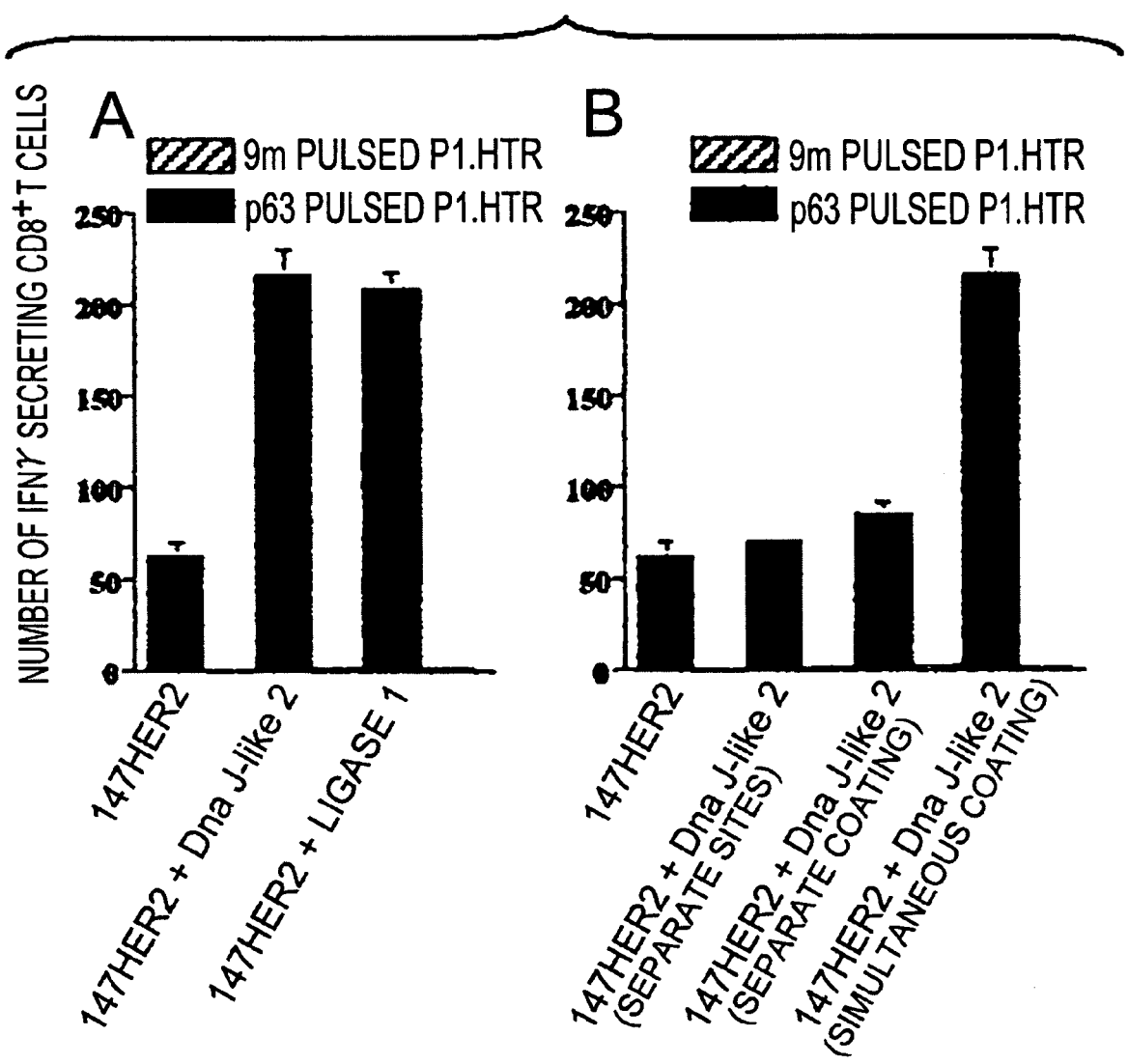
FIG. 4 depicts graphs showing that SEREX-defined molecules recognizing CD4$^+$ T cells co-presented with HER2 p63 peptide induce HER2 p63-specific CD8$^+$ T cells.

Enhancement of HER2-specific CD8$^+$ T Cell Induction by Immunogenic Wild-type Molecules A cDNA plasmid encoding 147 N-terminal amino acid residues of human HER2 (hereinafter referred to as 147HER2) was prepared. According to the method described in Example 2, 147HER2 was immunized together with a plasmid encoding Dna J-like 2 or ligase 1, or without plasmid coding any of the SEREX-defined molecules. The same target cell as in Example 2 was used and the number of IFNγ-secreting CD8$^+$ T cells was similarly counted. Increase in HER2 p63-specific CD8$^+$ T cells was observed by the co-immunization with either of the SEREX-defined molecules (FIG. 4, panel a). Data are represented by mean ±SEM of three experiments.

Similar to mERLK2 in Example 3, the increase of HER p63-specific CD8$^+$ T cells was examined in: (1) mice immunized with gold particles that were coated with both 147HER2 plasmid and SEREX-defined molecule plasmid; (2) mice immunized with individually coated gold particles; and (3) mice wherein the individually coated gold particles were respectively injected at distant parts of the abdomen (FIG. 4, panel b). Data are represented by mean ±SEM of three experiments. The increase in the number of p63-specific CD8$^+$ T cells was observed only for mice immunized with particles double-coated with plasmids of the two different molecules.

Considering this result with the result observed for mERK2 target tumor-specific immunity, it is strongly indicated that the immune response induced by immunogenic wild-type cellular molecules have the function to promote generation of CD8$^+$ T cells in anti-tumor immune response against various tumors.

EXAMPLE 7

In Vivo Tumor Rejection

After in vivo injection, CMS5 m tumor cell establishes metastases in the lungs, leading to death of animals within 5 to 6 weeks. Thus, BALB/c mice were challenged with 1×10$^6$ CMS5 m tumor cells in a total volume of 0.1 ml injected through the lateral caudal vein and used as models for pulmonary metastasis. Biweekly immunization with (1) plasmid encoding mERK2, (2) a mixture of mERK2 plasmid and control vector, or (3) a mixture of mERK2 plasmid and Dna J-like 2 plasmid, following the method described in Example 2 was commenced 7 or 14 days before, on the day of tumor challenge or 5 days after tumor challenge. After 28 days, mice were killed, and the number of pulmonary nodules was counted under a dissecting microscope. Each group included 5 animals, and the results are represented as mean±SEM of the 5 animals.

Figure 5:
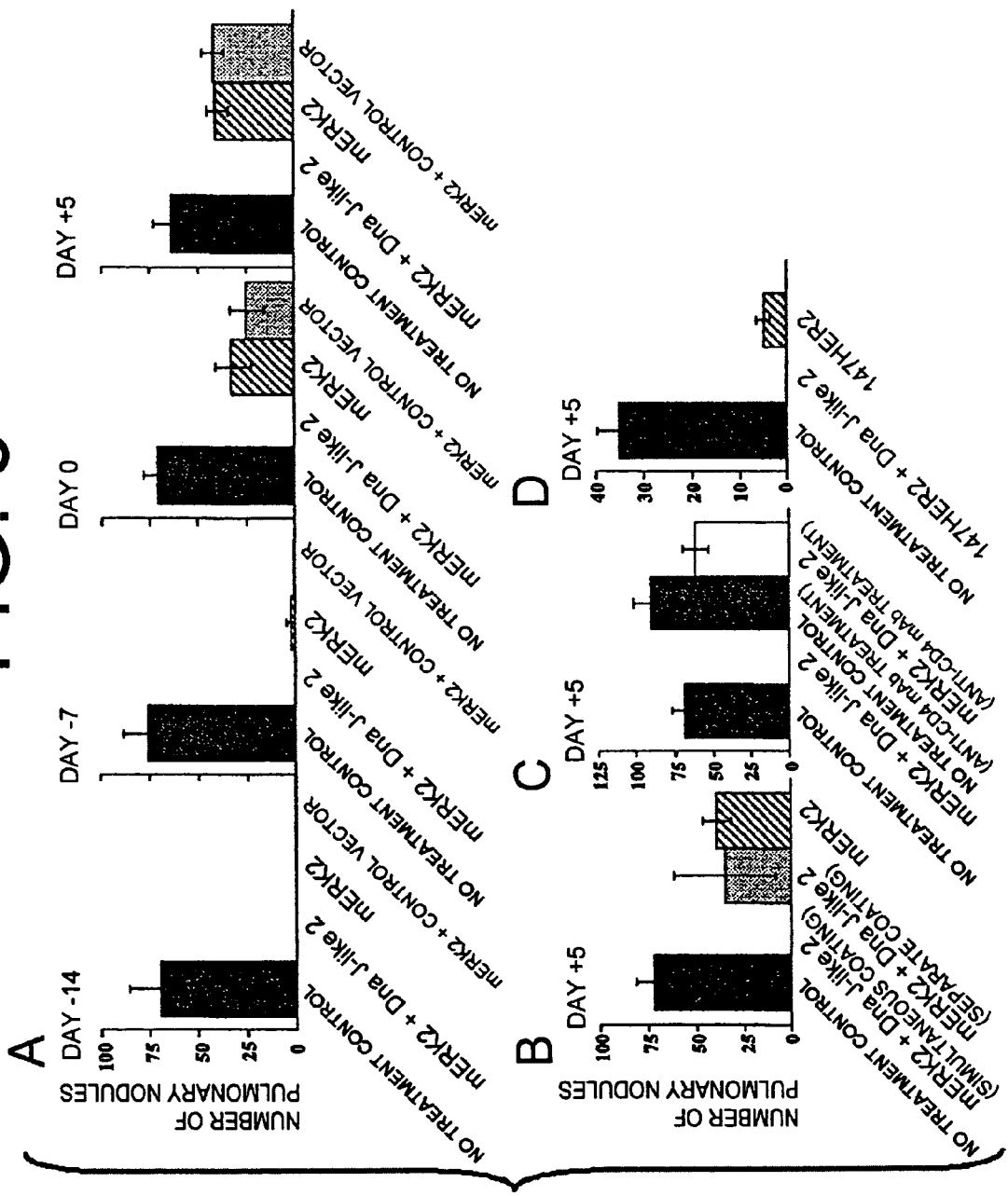
FIG. 5 depicts graphs showing in vivo preventive and therapeutic effects against pulmonary metastasis of immunization using mERK2 or 147HER2 and Dna J-like 2.

Immunization of mice with plasmid encoding mERK2 initiated 14 days before tumor challenge led to complete prevention of pulmonary metastasis. This protective effect was lost when immunization was initiated 7 days before tumor challenge or after tumor challenge (FIG. 5, panel a). In contrast, immunization using a combination of plasmids of mERK2 and Dna J-like 2 plasmids showed complete prevention of metastases even when initiated as late as 5 days after tumor challenge (FIG. 5, panel a). Absence of metastasis was confirmed by histopathological examination. The numbers in FIG. 5, panel a are expressed as mean ±SEM of the five mice in each group.

Next, similarly to the above method except for the use of gold particles coated together with mERK2 plasmid and Dna J-like 2 plasmid, and mixtures of separately coated gold particles, their therapeutic effects were determined by immunization of mice after 5 days from tumor challenge. Pulmonary metastasis was not completely suppressed when the separately coated gold particles were used. It was demonstrated that co-presentation of mERK2 and Dna J-like 2 on the same gold particle is required (FIG. 5, panel b). The numbers in FIG. 5, panel b are expressed as mean ±SEM of the five mice in each group.

Furthermore, according to the method described in Example 4, mice were treated with anti-CD4 mAb (GK1.5) and then, after 5 days of tumor challenge, were immunized with gold particles co-coated with mERK2 and Dna J-like 2 to examine its therapeutic effect. As a result, the therapeutic effect of mERK2 and Dna J-like 2 was lost due to the treatment by anti-CD4 mAb (GK1.5). This shows that the therapeutic effect of mERK2 and Dna J-like 2 is CD4$^+$ T cell-dependent (FIG. 5, panel c). The numbers in FIG. 5, panel c are expressed as mean ±SEM of the five mice in each group.

In addition, the therapeutic effects of plasmid encoding 147HER2, and a mixture of 147HER2 plasmid and Dna J-like 2 plasmid were examined by immunization of mice after 5 days of tumor challenge. The procedure was performed as described above except that the animals were sacrificed after 20 days of tumor challenge. As a result, similar to CMS5 mHE, increased therapeutic effect was observed (FIG. 5, panel d). The numbers in FIG. 5, panel d are expressed as mean ±SEM of the five mice in each group.

As stated above, pulmonary metastasis of tumors that could not be completely suppressed by immunization with T cell epitopes alone was completely inhabited by conducting immunization using plasmid encoding an antigen recognized by a CD4$^+$ helper T cell and plasmid encoding an antigen recognized by a CD$^+$ cytotoxic T cell coated the same particle.

EXAMPLE 8

HER2-specific CD8 Positive T Cell Enhancing Effect of Helper Epitope Included in NY-ESO-1

The following genes were used:
(a) 147HER2: a gene encoding the N-terminal 147 amino acid residues of c-erbB-2/HER2/neu(HER2);
(b) p63(T) mini gene: a gene encoding HER2p63(T), TYLPTNASL, alone;
(c) NY-ESO-1: a gene encoding NY-ESO-1, an antigen recognized by CD4$^+$ helper T cells; and
(d) mmIFN-γ: a gene encoding mouse interferon γ.

Each of the genes mentioned above were incorporated into the expression vector pCAGGS. The constructed expression vector was transformed into E. coli, and the vector was amplified and purified. Each of the purified expression vectors were adjusted to 1 μg/μl and coated on gold particles for immunization using Helios Gene Gun System (BioRad, Hercules, Calif.).

6 to 8 weeks old BALB/c mice (4 animals per group) were immunized twice with 2 weeks interval with the following combination of genes:

(Experiment 1)
(a) 147HER2
(b) 147HER2+mmIFN-γ
c) 147H 2+NY-ESO-1
d) 147HER2+mmIFN-γ+NY-ESO-1
Experiment 2)
a) p63(T) mini gene
b) p63(T) mini gene+mmIFN-γ
(c) p63(T) mini gene+NY-ESO-1
(d) p63(T) mini gene+mmIFN-γ+NY-ESO-1

One week after the final immunization, 2 animals per group were sacrificed and CD8 positive T cells were prepared from spleen using MACS system. Using P1.HTR (DBA/2 mice derived mastocytoma) pulsed with HER2p63(T) peptides as the target cell, ELISPOT assay was performed to detect mIFN-γ producing cells. P1.HTR pulsed with HER2p780 (PYVSRLLGI) peptides were used as negative control. Each experiment was conducted in duplicate. The result is shown in Table 2 and FIG. 6.

TABLE 2

|  | Ex.1 | Ex.2 | Ex.3 | Ex.4 |
| --- | --- | --- | --- | --- |
| p63(T) pulsed 200000 cells | 40.3 | 46 | 109.3 | 100.6 |
| p63(T) pulsed 100000 cells | 16.6 | 17.3 | 44 | 38 |
| p63(T) pulsed 50000 cells | 7 | 9 | 17.6 | 17 |
| p780 pulsed 200000 cells | 0.3 | 2 | 1 | 2.6 |
| p780 pulsed 100000 cells | 1 | 0.6 | 1 | 0.6 |
| p780 pulsed 50000 cells | 0.3 | 0.6 | 0.3 | 0.3 |

Ex.1; 147HER2 administered by gene gun 2×day7
Ex.2; 147HER2 + mIFN-γGG 2×day7
Ex.3; 147HER2 + NY-ESO-1 GG 2×day7
Ex.4; 147HER2 + mIFN-γ + NY-ESO-1 GG 2×day7

As a result, it was demonstrated that the combination of NY-ESO-1 and HER-2/neu significantly increases the number of mIFN-γ producing cells and induces tumor-specific immunity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications and publications cited herein are incorporated by reference.

What is claimed is:

1. A composition comprising two separate plasmid expression vectors, each comprising a nucleotide sequence that is operably linked to a promoter and that encodes an antigen, wherein, the first expression vector encodes (1) an antigen that is identified by the SEREX method, is restrictedly expressed on tumors and is recognized by a CD4+ helper T cell, the second expression vector encodes (2) a tumor-specific antigen or a tumor-associated antigen, which is recognized by a CD8+ cytotoxic T cell, and wherein the antigen encoded by the first expression vector and the antigen encoded by the second expression vector are different proteins.

2. The composition of claim 1, wherein the antigen encoded by the first vector is NY-ESO-1.

3. The composition of claim 2, wherein the composition further comprises an expression vector encoding interferon gamma.

4. The composition of claim 1, wherein the antigen encoded by the second vector is HER2 or HER-2/neu.

5. The composition of claim 4, wherein the composition further comprises an expression vector encoding interferon gamma.

6. The composition of claim 1, wherein the antigen encoded by the first vector is NY-ESO-1 and that encoded by the second vector is HER-2/neu.

7. The composition of claim 6, wherein the composition further comprises an expression vector encoding interferon gamma.

8. The composition of claim 1, wherein both of the expression vectors are immobilized on the same carrier.

9. The composition of claim 1, wherein the antigen encoded by the second vector is selected from the group consisting of MAGE, BAGE, GAGE, NY-ESO-1, CDK4, MUM-1, CASP-8, ras, bcr-abl, MART-1, TRP, tyrosinase, gp100, PSA, proteinase 3, HER2/neu, CEA, SART1, EBV, HPV, and HTLV-1.

10. The composition of claim 1, wherein the composition further comprises an expression vector encoding interferon gamma.

11. A composition comprising two separate plasmid expression vectors, each comprising a nucleotide sequence that is operably linked to a promoter and that encodes an antigen, wherein, the first expression vector encodes (1) an antigen recognized by a CD4+ helper T cell selected from the group consisting of Dna J-like 2, DNA ligase 1, galectin 1, poly(A) binding protein, Homo sapiens hexamethylene-bis-acetamide-inducible, human retinoic acid-responsive protein, H. sapiens hepatitis delta antigen interacting protein A (DIPA), H. sapiens cDNA FLJ20644 fis clone KATO02588, and NY-ESO-1, the second expression vector encodes (2) a tumor-specific antigen or a tumor-associated antigen, which is recognized by a CD8+ cytotoxic T cells and wherein the antigen encoded by the first expression vector and the antigen encoded by the second expression vector are different proteins.

12. The composition of claim 11, wherein the composition further comprises an expression vector encoding interferon gamma.

13. A vaccine comprising any one of the compositions described in claims 1, 2, 4, 8, 11, 9, 10, and 3.

14. A method for inducing tumor-specific immunity in a mammal, comprising the step of intradermally administering the composition of any one of claims 1, 2, 4, 8, 11, 9, 10 and 3 to the mammal using a gene gun, whereby tumor-specific immunity is induced in the mammal, thereby inhibiting tumor growth in the mammal.

15. A composition comprising first, second and third expression vectors, the first expression vector encoding (1) an antigen that is identified by the SEREX method and is recognized by a CD4+ helper T cell, the second expression vector encoding (2) a tumor-specific antigen or a tumor-associated antigen, which is recognized by a CD8+ cytotoxic T cell, and the third expression vector encoding (3) interferon gamma.

16. A composition comprising two separate plasmid expression vectors, each comprising a nucleotide sequence that is operably linked to a promoter and that encodes an antigen, wherein, the first expression vector encodes (1) an antigen recognized by a CD4+ helper T cell selected from the group consisting of Dna J-like 2 encoded by the nucleotide sequence of SEQ ID NO:2, DNA ligase 1, galectin 1, poly(A)

binding protein, *Homo sapiens* hexamethylene-bis-acetamide-inducible encoded by the nucleotide sequence of SEQ ID NO:3, human retinoic acid-responsive protein encoded by the nucleotide sequence of SEQ ID NO:4, *H. sapiens* hepatitis delta antigen interacting protein A (DIPA), *H. sapiens* cDNA FLJ20644 fis clone KATO02588 encoded by the nucleotide sequence of SEQ ID NO:1, and NY-ESO-1, the second expression vector encodes (2) a tumor-specific antigen or a tumor-associated antigen, which is recognized by a CD8+ cytotoxic T cell, and wherein the antigen encoded by the first expression vector and the antigen encoded by the second expression vector are different proteins.

* * * * *

SEQUENCE LISTING

<160> NUMBER OF SEQ ID NOS: 4

<210> SEQ ID NO 1
<211> LENGTH: 1781
<212> TYPE: DNA
<213> ORGANISM: Homo sapiens

<400> SEQUENCE: 1

```
aaaaatccgg cttggtgagc ttgggtcgcc tctgaaggag aaccattttc catctctttc      60 atagttttt  cccccagtca gcgtggtagc ggtattctcc gcggcagtga cagtaattgt     120
ttttgtctct ttagccaaga cttccgccct cgatcaagat ggtggttgga cggccttcct     180
aacctttacg gggcctggcg gtgctgacgc ctgagctggt aggggtggag caggtaggaa     240
acagcaaatg cagaagctgc tgcgcgggag tcggccatgg actggaaaga agttcttcgt     300
cggcgcctag cgacgcccaa cacctgtcca aacaaaaaaa aaagtgaaca agaattaaaa     360
gatgaagaaa tggatttatt tacaaaatat tactccgaat ggaaggagg  tagaaaaaac     420 acaaatgaat tctataagac cattccccgg ttttattata ggctgcctgc tgaagatgaa     480
gtcttactac agaaattaag agaggaatca agagctgtct ttctacaaag aaaaagcaga     540
gaactgttag ataatgaaga attacagaac ttatggtttt tgctggacaa acgccagaca     600
ccacctatga ttggagagga agcgatgatc aattacgaaa acttttttgaa ggttggtgaa     660 aaggctggag caaagtgcaa gcaatttttc acagcaaaag tctttgctaa actccttcat     720
acagattcat atggaagaat ttccatcatg cagttcttta attatgtcat gagaaaagtt     780
tggcttcatc aaacaagaat aggactcagt ttatatgatg tcgctgggca ggggtacctt     840
cgggaatctg atttagaaaa ctacatattg gaacttatcc ctacgttgcc acaattagat     900
ggtctggaaa aatctttcta ctcctttat  gtttgtacag cagttaggaa gttcttcttc     960
```

```
tttttagatc ctttaagaac aggaaagata aaaattcaag atattttagc atgcagcttc    1020
ctagatgatt tattggagct aagggatgag gaactgtcca aggagagtca agaaacaaat    1080
tggttttctg ctccttctgc cctaagagtt tatggccagt acttgaatct tgataaagat    1140
cacaatggca tgctcagtaa agaagaactc tcacgccatg aacagctac  catgaccaat    1200 gtcttcttag accgtgtttt ccaggagtgt ctcacttatg atggagaaat ggactataag    1260
acctacttgg actttgtcct tgcattagaa acagaaagg  aacctgcagc tctacaatat    1320
attttcaaac tgcttgatat tgagaacaaa ggatacctga atgtcttttc acttaattat    1380
ttctttaggg ccatacagga actaatgaaa atccatggac aagatcctgt ttcatttcaa    1440
gatgtcaagg atgaaatctt tgacatggta aaaccaaagg atcctttgaa aatctctctt    1500
caggatttaa tcaacagtaa tcaaggagac acagtaacca ccattctaat cgatttgaat    1560
ggcttctgga cttacgagaa cagagaggct cttgttgcaa atgacagtga aaactctgca    1620
gaccttgata tacatgatc  tctgaaagac tagactgtct tatattatga gatacttgaa    1680
tgctgcatgt aaagccttta aagcaaaatc ctcagaaatg gtctaaataa aacacttgat    1740
atgcctagag aacacaaaaa aaaaaaaaaa aaaaaaaaa  a                        1781

<210> SEQ ID NO 2
<211> LENGTH: 2242
<212> TYPE: DNA
<213> ORGANISM: Mus musculus
<220> FEATURE:
<221> NAME/KEY: misc_feature
<222> LOCATION: (1328)..(1328)
<223> OTHER INFORMATION: n is a, c, g, or t

<400> SEQUENCE: 2
gtgggtggtg gaggagcagc gtgtggctga gctgcgctgt gctccggtcc tttccgctct      60
ccggcgccgg cccgctcacc ggctgtaaaa aatggtgaaa gaaaccactt actacgatgt     120
tttgggggta aacccaatg  ccacccagga agaattgaaa aaggcatata gaaaattggc     180
cttgaagtac caccctgata agaatccaaa tgaaggagaa agtttaaac  agatttctca     240 agcttatgaa gttcttgctg attccaaaaa aagggaacta tatgataaag gaggggagca     300
ggcgattaaa gagggcggag caggtggtgg ttttggctca cccatggata tctttgatat     360
gttctttgga ggaggaggaa gaatgcaaag agaaaggaga ggtaaaaatg ttgttcatca     420
gctctcagtg accttagaag acttatataa tggtgcaaca agaaaactgg ctctgcaaaa     480
gaatgtgatt tgtgacaaat gtgaaggccg aggtggtaag aaaggagcag tagagtgctg     540
tcccaactgc cggggacag  gtatgcagat aaggattcat cagattggac caggaatggt     600
tcagcaaatt cagtcagtgt gcatggagtg ccagggtcat ggagaacgca tcagtccaaa     660
agacagatgt aaaagctgca atggaagaaa atagttcga  gagaagaaaa ttttagaagt     720
tcatattgat aaaggcatga agatggtca  gaagataaca ttccacggtg aaggagacca     780
agaaccagga ctggagccag gagatattat cattgtgtta gatcagaagg accatgctgt     840
ttttacaagg cgaggagaag accttttcat gtgtatggac atacagctgg ttgaagcatt     900
gtgcggcttc caaaagccaa tatctactct tgacaaccga accatagtca tcacctctca     960
tccaggtcag attgtcaagc atgggtatat aaaatgtgtg ctaaatgaag gtatgccaat    1020
ataccgtcgg ccatatgaaa agggacgtct aatcattgag tttaaggtaa actttcctga    1080
aaatggcttt ctctcctg   ataaaactctc tttgctggaa aaactccttc ctgaaaggaa    1140
ggaagtagaa gagactgatg aaatggatca ggtagaactg gtggactttg atccaaatca    1200
```

```
ggaaagacgg cgtcattata atggagaagc gtatgaggat gatgaacatc accccagagg      1260
tggcgttcag tgtcagacct cttaatgggc cagtcactct ttgacattct gtatgcagta      1320
gtgaatgngg gaaggactgt aatcataata agctcactac ttggctattg tttttgtttt      1380
aatattcaac tatagtagtg ttttaaaaaa agttaaatga agaataaaca caaatataaa      1440
agctctgact ttgccctgta tgtatgatga cttcagtgtt caagatgaaa atgaatactt      1500
gtaaaaacta gtttaaaaag ttccctagca tctgttaggt catatcttgt gtaactgata      1560
atagctgtgt acattagact gacatgctag gtatgtgttg tatgacccct cattgttaag      1620
ctatgggatt aaaattctgt atttaactgg taatcaaaag aaaacaatta gttacatgtc      1680
ggtctgtcta gttatatgaa gtgaaccaat tgtgatgcct ttgcattgta ttgcctcagc      1740
cattactaga aggtggcata atacatttcg cctgtgttat tagtgataga aatgattcat      1800
tcctaaagaa gtttatcata agctactgct taagggcttg ctcttctaga ttgcatcccc      1860
ttctgctgtg caattttaa gatatatata taaacagaaa acatgatcac cttttccc      1920 ttctcaaacc atgataagcc cttgcttggg tgtagtgact ccaaagccc aagtaactta      1980 caaatgaaag tgatgagatc tgtacgtgga ggggtgattt gcatgtataa tccagggaag      2040
gtgctcctta ggtctgttcc aggctttcta ttcgacttag gctccaacgt aactgcaatt      2100
taatgttggt agtatagcaa attatgaata gatttgttgt atgttttgaa gtcacatgct      2160
tacatgctta aatctggata tcagaattta agcagttact gaaatgtatg gctgtctaat      2220
atactgatta caaagtgtta aa                                               2242

<210> SEQ ID NO 3
<211> LENGTH: 3601
<212> TYPE: DNA
<213> ORGANISM: Homo sapiens

<400> SEQUENCE: 3
gcaggttggg agggaaagtc gggggaggac gcggaagagg agctgtggga aggggaggga       60
gggagggagg aaaagaggag gaggcggagg agaactgagc agagcagagc atcgagccaa      120
aggggagatg agtttgtctg tcctctgctg aggctacggc cgggcctagg gaactgggag      180
cttgggtgga agcgacaccc gtggaagtgg gaggaggtgg cgccgggact ttaaccctt       240 gtgggctctg cggcagggga tttaaccctt tgtggatctg gccctcgga ggcagcgtca      300 tcggtagttt taacccttc ggggctgggt ttcacgcact ggacttaccc tcatcacctt      360
gctcaccaac tcctttattg gggtgctccg cttggaggtt tgaggcccac ctccgcccat      420
tacgtactgt tcctgccgct gcaccccctt ggacccgcta gctggccgca ctgtgggcgc      480
ttaacccttt actgacttga gctccccaga ttgcagttgg agtttgctga tagaaggact      540
agctaaaggc gtcactgcag gaattacaaa ctgaagagga ctctgttgga ctgttttttt      600 tttcttttt ttttttttt aagaaaaacc cattttttc cttaaggact tactagccaa      660
aatttcttaa acttcgagga ctctactagc catggccgag ccattcttgt cagaatatca      720
acaccagcct caaactagca actgtacagg tgctgctgct gtccaggaag agctgaaccc      780
tgagcgcccc ccaggcgcgg aggagcgggt gccgaggag acagtaggt ggcaatcgag      840 agcgttcccc cagttgggtg gccgtccggg gccgaggggg aagggagcc tggaatccca      900 accacctccc ttgcagaccc aggcctgtcc agaatctagc tgcctgagag agggcgagaa      960
gggccagaat ggggacgact cgtccgctgg cggcgacttc ccgccgccgg cagaagtgga     1020
```

-continued

```
accgacgccc gaggccgagc tgctcgccca gccttgtcat gactccgagg ccagtaagtt    1080
gggggctcct gccgcagggg gcgaagagga gtggggacag cagcagagac agctggggaa    1140
gaaaaaacat aggagacgcc cgtccaagaa gaagcggcat tggaaaccgt actacaagct    1200
gacctgggaa gagaagaaaa agttcgacga gaaacagagc cttcgagctt caaggatccg    1260
agccgagatg ttcgccaagg gccagccggt cgcgccctat aacaccacgc agttcctcat    1320
ggatgatcac gaccaggagg agccggatct caaaaccggc ctgtactcca agcgggccgc    1380
cgccaaatcc gacgacacca gcgatgacga cttcatggaa gaaggggtg aggaggatgg    1440
gggcagcgat gggatgggag gggacggcag cgagtttctg cagcgggact ctcggagac    1500
gtacgagcgg taccacacgg agagcctgca gaacatgagc aagcaggagc tcatcaagga    1560
gtacctggaa ctggagaagt gcctctcgcg catggaggac gagaacaacc ggctgcggct    1620
ggagagcaag cggctgggtg gcgacgacgc gcgtgtgcgg gagctggagc tggagctgga    1680
ccggctgcgc gccgagaacc tccagctgct gaccgagaac gaactgcacc ggcagcagga    1740
gcgagcgccg cttttccaagt ttggagacta gactgaaact ttttggggg aggggcaaa    1800
gggggacttt tacagtgatg gaatgtaaca ttatatacat gtgtatataa gacagtggac    1860
ctttttatga cacataatca gaagagaaat ccccctggct ttggttggtt tcgtaaattt    1920
agctatatgt agcttgcgtg cttctcctg ttcttttaat tatgtgaaac tgaagagttg    1980
cttttcttgt tttccttttt agaagttttt ttccttaatg tgaaagtaat ttgaccaagt    2040
tataatgcat ttttgttttt aacaaatccc ctccttaaac ggagctataa ggtggccaaa    2100
tctgagaaca attaaattca ttttagttat aataaattta atatttgtaa atgtaacata    2160
gtttcagtgt gattctaga gctaattcaa aatagtattg atatatttta tgtgactgca    2220
tttttgggga ggggtaccga aatcgttaaa tttgtcagtt tgcaaaaata tcaatcttta    2280
atgggagaat tttcaatttg ccaatttttt ccttgaatgg gtttaagtat gctacaatat    2340
acagttcagg caaaatttaa gatgtaatta tcttcaatac ttaagtgtgc ttgctttcta    2400
gtgccttggt tttctttctt gatgctggaa aaataaacaa accggtattg agtgtttagg    2460
cgagtggaaa gtggctacaa tccaaaattt taaatttaac tctgcctcgg ccattcaaaa    2520
gtctaataac aaaaaatgta aacctaattt ggcagtttgt taggttagac aactgacagc    2580
ctcatttcat tcctacaagt tggttttcag taatctcttc cttcccccta gtaaggctgg    2640
aagaggctct tggcaaactt cttagtgcaa gcaatggtta gattaatttg tgaggcagct    2700
cttttaagacg ttcagaggta agaaatactg gatttataaa gcaaatggct gtttggggga    2760
ttccaaggat ttacctaatt gtccaattct acgtgctctc tataccaaaa caaaaaaaaa    2820
aagctatcca ccttttccatg tgggtcaaac taaaattaga aatgtcccct cactgcagat    2880
caaatgtaaa gcttccagtt aaggagctaa atgaggtcct cagctgaatg aggaaccctg    2940
tacatcccct tgcacagccc tattctaaat cgcttaaact atgctgatag ctgcttaggt    3000
tcttgagtag ttctgctctt aaacgtaggg aggccctgag aactaaattt tgccccaaaa    3060
taaaaacaga aattatgaga ttgcctcctg tcatttggt taacccagtc cttcacctgc    3120
cctgtgtcag tgtcttctga gggcaattgc gttgctcaaa tcactagcac agaggttcct    3180
taatttgggg ccttagaaac cattgtgggc cttgggtcc atgaacccca tgaaattatt    3240
tgtagacttg tatgtacatt tttctgggga gaaggttcaa gagattcata agattgtcaa    3300
actccttgaa ggttcagaac ctctgcaggg aaggggaag aaaaccctcc cattaggaag    3360
catgcttttg cagttaaatg gcgatggtgg aggtgatagg gacttcaaga gtaaaatgca    3420
```

-continued

| | |
|---|---|
| ccttgtattg cataagaagc atacacaaat caataaatca agggagatta taccagtagg | 3480 |
| actgaatcag ggccttcaaa gctggactga gttggtcctg ttctggcaca tatggtccac | 3540 |
| tggagacaat gtatgattga gttttctttt ggtctaaaaa ttatattaaa catttatttt | 3600 |
| g | 3601 |

<210> SEQ ID NO 4
<211> LENGTH: 2520
<212> TYPE: DNA
<213> ORGANISM: Homo sapiens

<400> SEQUENCE: 4

| | |
|---|---|
| gccgtgttct ccttctgcgt gggcgtggcg ggccgcgcgc gggtctccgt ggaagtccgt | 60 |
| ttcgtgagca gcgccaaggg aaaggggctg tttgccacac agctcatccg gaaggggag | 120 |
| accatcttcg tagaacggcc cctggtggct gcacagtttc tctggaatgc actttatcgc | 180 |
| taccgagcct gtgaccactg ccttagggca ctagagaagg cagaggagaa tgcccagagg | 240 |
| ctgaccggga aaccaggcca ggttctgcct cacccagagc tgtgcactgt gcgcaaagac | 300 |
| ctccaccaga actgtcccca ttgccaagtg atgtactgca gtgcagaatg tcggttggca | 360 |
| gccactgagc aataccacca ggtcctgtgc ccaggcccct cccaggatga ccccttgcat | 420 |
| cctctcaata gcttcaggga ggcatggagg agtattcact acccacctga gactgcaagc | 480 |
| atcatgttga tggctaggat ggtggccaca gtgaagcagg cgaaggacaa ggaccgttgg | 540 |
| atcagactct tttcccagtt tgtaacaaa acagccaatg aagaggagga aattgtccat | 600 |
| aaacttctgg gagacaaatt caagggccaa ctggaacttc tgcggagact cttcacagag | 660 |
| gccctctatg aggaagcagt cagccagtgg ttcactccag atggattccg gtctctcttt | 720 |
| gctcttgttg ggaccaatgg ccaaggaatc gggaccagct ccctaagcca gtgggtccat | 780 |
| gcctgtgaca ctctggagtt gaagcctcag gaccgtgagc acgttgacgc cttcattgac | 840 |
| cagctataca aggacatcga ggcagcaact ggagagtttc ttaactgtga aggatctggc | 900 |
| ctctttgtgc ttcagagctg ctgcaaccac agttgtgtgc ccaatgcaga gacctccttt | 960 |
| ccagaaaaca acttcctttt gcatgtcact gctctggagg atattaagcc aggagaggaa | 1020 |
| atttgtatca gctacttgga ctgctgtcag cgggagcgca gccgccacag ccgccacaag | 1080 |
| atcctcaggg agaactatct atttgtctgt tcctgtccca atgcctggc agaggctgat | 1140 |
| gaacccaatg tgacctcaga agaggaagag gaagaggagg aggaggagga aggagagcca | 1200 |
| gaagatgcag agctggggga tgagatgact gatgtgtgat gttgccctgc ccagaaaggg | 1260 |
| ccctgcccta gaccctgcca gaaaggggg ctcttccccc agagaagtgg cttggaggga | 1320 |
| acttcccact cccattgcct gctttcccca ttccagccct ctctgctaga gggtaggaga | 1380 |
| gagcctggat ctctggcccc aaccccacc agacctcatg ccctgacac tgctgctgag | 1440 |
| ttggctcaga ctctgcactg gcactgagcc tttcacaact ggcctcccct tgaggttcct | 1500 |
| ccactctagg gtttgagggg ctggaatcag ggccagggcc taacagtgtt tcttcccctc | 1560 |
| ggccccacgg cccatactca ccccttcacc tgaggcttct ccctctcaa cttgctgttg | 1620 |
| atttctttg aggggtaaaa gaaagaccga gttcattgaa gcagagatgg gaggtggtga | 1680 |
| ggcgtcctca cctccccca ccacagctgt ggctggtaag gcaactgctt gaccactggc | 1740 |
| ccagcaagca gaggcgggca ggaggatctg ggcatcctga gcccttccc tgaggctgtc | 1800 |
| tcctgggaat gctggaccag ggggattact tccccccacc acacccccat ttggacatct | 1860 |

-continued

```
ggggaagtgg agattaaccc tcccccagac tcgtgccttg cctctcagga cctggcacag    1920
tggctggcct tatggagtat ggaaaaggcc tctgccttcc tcaggaggga cacatagtgg    1980
gtcatcaccc tttctcacac ctgcttccca atgagcactc agcagcatgg ctgagacctg    2040
gggcttgaca ggcctgcgct ccttagatta ggatgctctg gtattcctgg ggccagttaa    2100
aatgggtcag tgagggctc tcctggcctc aatctccatc tttagggtct ccacagacta    2160
acattgaagt cttccagaaa cctcgaggag ctgggctaga tacttcgaga gtagccctgt    2220
cttgtcccct cctaccccca gattagcacc accctctca ctcttgggtt ggatgctatg    2280
ggaattacaa cccatcactc ccaatgcctc cctttcctgg aggagcctgc tgcattctcc    2340
tgctgaggga tcccagagag ggcaggtgcc cacccacag gcccttttcct ggaccatgga    2400 gccaggtgaa acctgtctgg cccccttaccc attgggttct tactccttca caacggtcag    2460
cactcctctc ccagccccc tgcccactgt tctcaataaa atgtgagtgg tgaaaaaaaa    2520
```